(12) United States Patent
Daniel et al.

(10) Patent No.: US 7,008,421 B2
(45) Date of Patent: *Mar. 7, 2006

(54) APPARATUS AND METHOD FOR TISSUE RESECTION

(75) Inventors: Steven A. Daniel, Fremont, CA (US); David L. Morris, Lugarno (AU)

(73) Assignee: Resect Medical, Inc., Fremont, CA (US)

( * ) Notice: Subject to any disclaimer, the term of this patent is extended or adjusted under 35 U.S.C. 154(b) by 148 days.

This patent is subject to a terminal disclaimer.

(21) Appl. No.: 10/413,112

(22) Filed: Apr. 14, 2003

(65) Prior Publication Data

US 2004/0039429 A1   Feb. 26, 2004

Related U.S. Application Data

(60) Provisional application No. 60/405,051, filed on Aug. 21, 2002.

(51) Int. Cl.
*A61B 18/18* (2006.01)

(52) U.S. Cl. .......................... 606/50; 606/41; 607/101

(58) Field of Classification Search .................. 606/41, 606/42, 48–50; 607/101, 102
See application file for complete search history.

(56) References Cited

U.S. PATENT DOCUMENTS

| 3,991,770 A | 11/1976 | LeVeen |
|---|---|---|
| 4,154,246 A | 5/1979 | LeVeen |
| 4,411,266 A | 10/1983 | Cosman |
| 5,231,995 A | 8/1993 | Desai |
| 5,246,438 A | 9/1993 | Langberg |
| 5,366,490 A | 11/1994 | Edwards |
| 5,370,675 A | 12/1994 | Edwards |
| 5,403,311 A | 4/1995 | Abele |
| 5,421,819 A | 6/1995 | Edwards |
| 5,458,597 A | 10/1995 | Edwards |
| 5,470,309 A | 11/1995 | Edwards |
| 5,472,441 A | 12/1995 | Edwards |
| 5,480,397 A | 1/1996 | Eggers |
| 5,484,400 A | 1/1996 | Edwards |
| 5,486,161 A | 1/1996 | Lax |
| 5,531,676 A | 7/1996 | Edwards |
| 5,536,267 A | 7/1996 | Edwards |
| 5,542,916 A | 8/1996 | Hirsch |
| 5,556,377 A | 9/1996 | Rosen |
| 5,573,533 A | 11/1996 | Strul |
| 5,599,345 A | 2/1997 | Edwards |
| 5,599,346 A | 2/1997 | Edwards |
| 5,609,151 A | 3/1997 | Mulier |

(Continued)

*Primary Examiner*—Michael Peffley
(74) *Attorney, Agent, or Firm*—Courtney Staniford & Gregory LLP

(57) ABSTRACT

A tissue ablation system is described that generates a uniform avascular plane of coagulated tissue to aid in the bloodless or near-bloodless resection of various biological tissues from a variety of organs. The tissue ablation system includes an energy director guide and two or more sets of bipolar energy directors. The energy director guide includes a series of channels that configure the energy directors to provide approximately uniform power distribution or current density through a target tissue volume or plane. The spacing among the channels of the energy director guide varies according to the total number of energy directors received in the energy director guide so that relative spacing among the center-most channels is largest and relative spacing among the end-most channels is smallest. The energy director guide secures a selected position of each of the energy directors in the target tissue volume.

28 Claims, 19 Drawing Sheets

U.S. PATENT DOCUMENTS

| | | |
|---|---|---|
| 5,672,173 A | 9/1997 | Gough |
| 5,672,174 A | 9/1997 | Gough |
| 5,697,909 A | 12/1997 | Eggers |
| 5,720,719 A | 2/1998 | Edwards |
| 5,722,975 A | 3/1998 | Edwards |
| 5,728,143 A | 3/1998 | Gough |
| 5,735,847 A | 4/1998 | Gough |
| 5,782,827 A | 7/1998 | Gough |
| 5,800,484 A | 9/1998 | Gough |
| 5,810,804 A | 9/1998 | Gough |
| 5,817,092 A | 10/1998 | Behl |
| 5,827,276 A | 10/1998 | LeVeen |
| 5,855,576 A | 1/1999 | LeVeen |
| 5,863,290 A | 1/1999 | Gough |
| 5,865,788 A | 2/1999 | Edwards |
| 5,868,740 A | 2/1999 | LeVeen |
| 5,913,855 A | 6/1999 | Gough |
| 5,925,042 A | 7/1999 | Gough |
| 5,928,159 A * | 7/1999 | Eggers et al. ............... 600/547 |
| 5,947,964 A | 9/1999 | Eggers |
| 5,954,717 A | 9/1999 | Behl |
| 5,957,961 A | 9/1999 | Maguire |
| 5,980,517 A | 11/1999 | Gough |
| 5,993,447 A | 11/1999 | Blewett |
| 6,001,095 A * | 12/1999 | de la Rama et al. .......... 606/41 |
| 6,007,499 A | 12/1999 | Martin |
| 6,016,452 A * | 1/2000 | Kasevich .................... 607/101 |
| 6,050,992 A | 4/2000 | Nichols |
| 6,059,780 A | 5/2000 | Gough |
| 6,080,149 A | 6/2000 | Huang |
| 6,090,105 A | 7/2000 | Zepeda |
| 6,123,701 A * | 9/2000 | Nezhat ........................ 606/33 |
| 6,212,433 B1 | 4/2001 | Behl |
| 6,235,023 B1 | 5/2001 | Lee |
| 6,241,725 B1 | 6/2001 | Cosman |
| 6,312,426 B1 | 11/2001 | Goldberg |
| 6,312,428 B1 | 11/2001 | Eggers |
| 6,337,998 B1 | 1/2002 | Behl |
| 6,358,246 B1 | 3/2002 | Behl |
| 6,419,673 B1 * | 7/2002 | Edwards et al. .............. 606/41 |
| 6,428,538 B1 | 8/2002 | Blewett |
| 6,471,695 B1 * | 10/2002 | Behl ........................... 606/32 |
| 6,530,922 B1 | 3/2003 | Cosman |
| 6,628,990 B1 * | 9/2003 | Habib et al. ................ 607/101 |
| 6,638,275 B1 * | 10/2003 | McGaffigan et al. .......... 606/41 |
| 2002/0120260 A1 * | 8/2002 | Morris et al. ................. 606/41 |

* cited by examiner

| | Values with Balanced Circuit 480 | | | | |
|---|---|---|---|---|---|
| | Zone 1 | Zone 2 | Zone 3 | Zone 4 | Zone 5 |
| | 219.5 | 200.1 | 167 | 200.1 | 219.5 |
| | 18.86 | 20.69 | 24.79 | 20.69 | 18.86 |
| | 7.235 | 19.56 | 24.79 | 19.56 | 7.235 |
| | | 7.935 | 23.45 | 7.935 | |
| | | | 9.51 | | |
| 482 — Total Power per Zone | 245.595 | 248.285 | 249.54 | 248.285 | 245.595 |
| % Error per Zone | 0 | -1.095299 | -1.606303 | -1.095299 | 0 |
| "Spacing" Value per Zone | 12.4 | 13.6 | 16.3 | 13.6 | 12.4 |
| 484 — "Spacing" Ratio per Zone | 1.00 | 1.097 | 1.315 | 1.097 | 1.00 |
| 486 — "Spacing" Ratio per Zone | 0.760736 | 0.834356 | 1 | 0.834356 | 0.760736 | 4.190184 |

Values with Balanced Circuit — 580

| | Zone 1 | Zone 2 | Zone 3 | Zone 4 | Zone 5 | Zone 6 | Zone 7 |
|---|---|---|---|---|---|---|---|
| | 503.1 | 445.6 | 354.5 | 380.4 | 354.5 | 445.6 | 503.1 |
| | 39.96 | 45.11 | 56.71 | 16.82 | 18.05 | 14.36 | 12.71 |
| | 12.71 | 14.36 | 18.05 | 38.43 | 41.24 | 45.11 | 39.96 |
| | 7.097 | 37.91 | 41.24 | 16.82 | 18.05 | 37.91 | 7.097 |
| | | 13.78 | 18.05 | 44.41 | 56.71 | 13.78 | |
| | | 8.013 | 47.65 | 44.41 | 47.65 | 8.013 | |
| | | | 17.33 | 16.15 | 17.33 | | |
| | | | 10.07 | 9.387 | 10.07 | | |
| 582 — Total Power per Zone | 562.87 | 564.77 | 563.60 | 566.83 | 563.60 | 564.77 | 562.87 |
| % Error per Zone | 0.00 | 0.34 | 0.13 | 0.70 | 0.13 | 0.34 | 0.00 |
| "Spacing" Value per Zone | 31 | 35 | 44 | 41 | 44 | 35 | 31 |
| 584 — "Spacing" Ratio per Zone | 1.000 | 1.129 | 1.419 | 1.323 | 1.419 | 1.129 | 1.000 |
| 586 — "Spacing" Ratio per Zone | 0.704545 | 0.795455 | 1 | 0.931818 | 1 | 0.795455 | 0.704545 |

FIG. 5C

| | Values with Balanced Circuit ⌒680 | | | | |
|---|---|---|---|---|---|
| | Zone 1 | Zone 2 | Zone 3 | Zone 4 | Zone 5 |
| | 133<br>39.36<br>24.18 | 118.7<br>39.36<br>38<br>24.18 | 105.7<br>39.36<br>39.36<br>38<br>24.18 | 118.7<br>39.36<br>38<br>24.18 | 133<br>39.36<br>24.18 |
| Total Current per Zone | 196.54 | 220.24 | 246.6 | 220.24 | 196.54 |
| "Spacing" Value per Zone | 12.4 | 13.9 | 15.6 | 13.9 | 12.4 |
| 682 ⌒ Current Density per Zone | 15.85 | 15.8446 | 15.80769 | 15.8446 | 15.85 |
| % Error | 0.0 | 0.0 | 0.3 | 0.0 | 0.0 |
| 684 ⌒ "Spacing" Ratio per Zone | 1.00 | 1.12 | 1.26 | 1.12 | 1.00 |
| 686 ⌒ "Spacing" Ratio per Zone | 0.79 | 0.89 | 1.00 | 0.89 | 0.79 |

FIG. 6C

APPARATUS AND METHOD FOR TISSUE RESECTION

RELATED APPLICATION

This application claims the benefit of U.S. Provisional Application No. 60/405,051, filed Aug. 21, 2002, which is currently pending.

TECHNICAL FIELD

This invention relates generally to an apparatus and method that aids in the resection of tissue, and more particularly to the bloodless or near bloodless resection of tissue.

BACKGROUND

Standard surgical procedures for trauma, cancer and transplants in the kidney, liver, and like organs have several key shortcomings affecting efficacy, morbidity and mortality. In an effort to fully remove or resect an organ, the surgeon may be forced to breach the tissue causing a large amount of bleeding. Careful hemostasis can minimize blood loss and complications but is laborious and time consuming using the systems and methods known in the art. Uncontrollable bleeding, for example, is one of the leading causes that prevent such treatments from being offered to patients with cirrhotic livers. In cancer patients, the surgeon must exercise care in an attempt not to allow any tumor cells to remain at a site of resection since any viable tumor cells may cause a recurrence of the cancer and negate the benefit of the procedure. Furthermore, surgeons can reduce the risk of complications by performing these procedures in an expedient manner to minimize anesthesia time and blood loss.

Typical methods for creating resections or controlling bleeding and blood loss include scalpels, electrocautery, ultrasonic scalpels, argon beam coagulators, and radio frequency (RF) surface dissectors. However, these therapies in their present form have several critical drawbacks including: (i) a complete lack or partial inability to create a hemostatic or near-hemostatic resection plane with any significant depth; (ii) a partial or complete lack of ability to make the tissue resection plane unable to support the growth of cancer cells left on the surface; (iii) a partial or complete lack of ability to kill cancerous cells remaining from an in adequate resection margin; (iv) an ability to reduce the operative time and likewise the complications resulting from the prolonged exposure to anesthesia; and (v) an ability to reduce the level of skill required to perform a safe and effective resection thereby allowing a greater availability of the treatment to the patient population.

BRIEF DESCRIPTION OF THE FIGURES

FIG. 4C is a table including power dissipation and spacing information corresponding to an energy director configuration providing balanced energy, under the embodiment of FIG. 4A.

FIG. 5B shows a table including power dissipation values corresponding to an energy director configuration providing balanced energy, under the embodiment of FIG. 5A.

FIG. 5C is a table including power dissipation and spacing information corresponding to an energy director configuration providing balanced energy, under the embodiment of FIG. 5A.

FIG. 6C is a table including current and spacing information corresponding to an energy director configuration providing balanced energy, under the embodiment of FIG. 6A.

Figure 1:
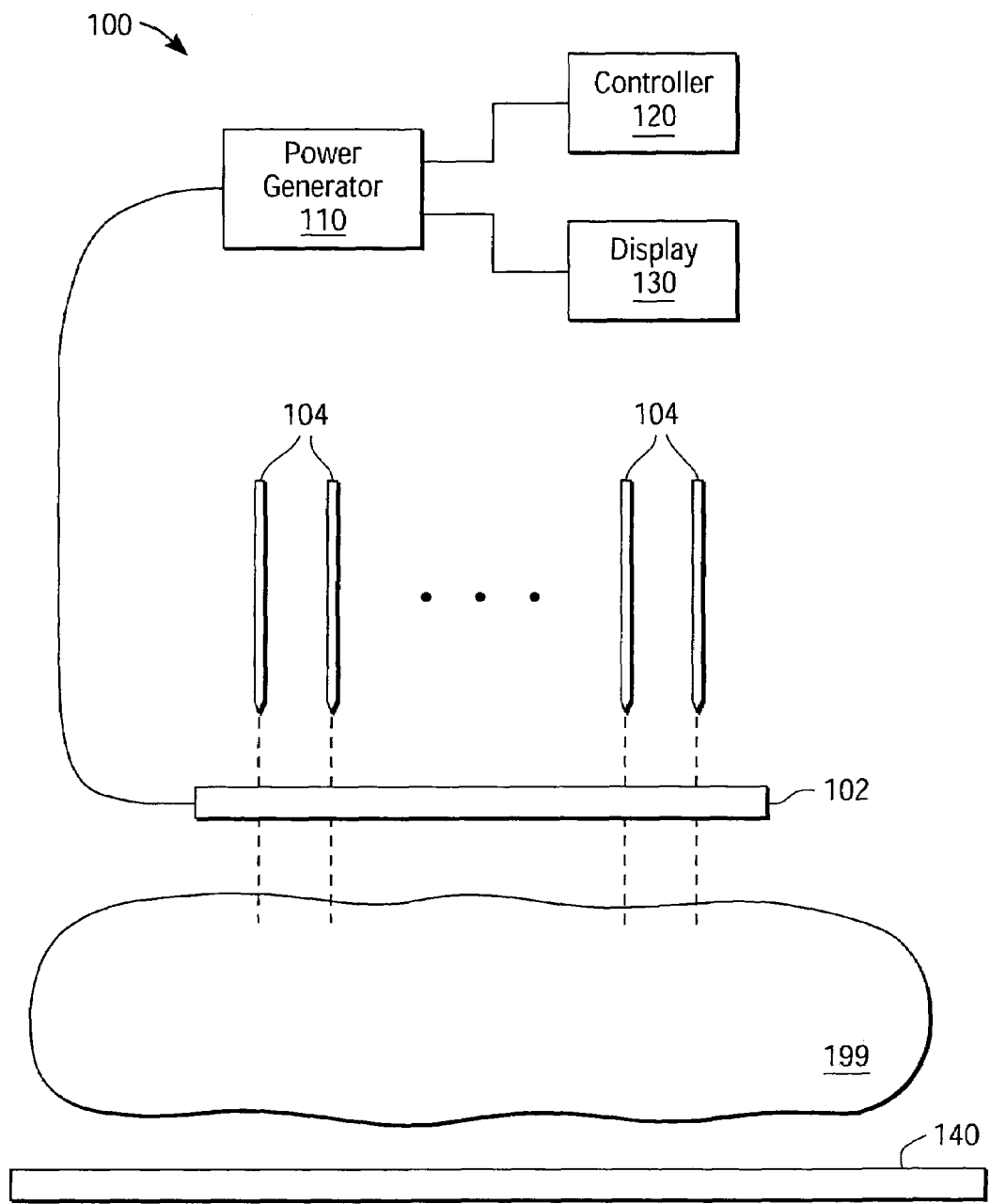
FIG. 1 is a tissue ablation system, under an embodiment.

In the drawings, the same reference numbers identify identical or substantially similar elements or acts. To easily identify the discussion of any particular element or act, the most significant digit or digits in a reference number refer to the Figure number in which that element is first introduced (e.g., element 102 is first introduced and discussed with respect to FIG. 1).

DETAILED DESCRIPTION

A tissue ablation system including numerous components and methods is described in detail herein. The tissue ablation system generates an avascular volume of coagulated tissue that aids in the bloodless or near-bloodless resection of various biological tissues from a variety of organs including, for example, the liver, spleen, kidney, and various other organs of the body. In the following description, numerous specific details are introduced to provide a thorough understanding of, and enabling description for, embodiments of the invention. One skilled in the relevant art, however, will recognize that the invention can be practiced without one or more of the specific details, or with other components, systems, etc. In other instances, well-known structures or operations are not shown, or are not described in detail, to avoid obscuring aspects of the invention.

FIG. 1 is a tissue ablation system 100, under an embodiment. The tissue ablation system 100 includes an energy director guide 102, or guide, and two or more pair 104 of bipolar energy directors, also referred to as electrodes. Alternative embodiments of the tissue ablation system 100 can include monopolar energy directors and various combinations of bipolar and monopolar energy directors. The energy directors 104 are configured for insertion into a volume of biological tissue 199. The energy director guide 102 configures the energy directors to provide approximately uniform power or energy distribution through a tissue volume, referred to as the target tissue or target tissue volume. The target tissue volume includes the volume within an approximately one (1) centimeter (cm) radius around each energy director 104 extending over the conducting length of the energy director 104, but is not so limited. The target tissue volume forms at least one plane of coagulated tissue.

The energy director guide 102 and the energy directors 104 are coupled among at least one generator 110, or power source, but are not so limited. The energy directors 104 of an embodiment couple to the generator 110 via the energy director guide 102. Alternatively, the energy directors 104 can couple directly to the generator 110 via a wire, cable, or other conduit.

Using the bipolar configuration of the energy directors 104, one electrode of an electrode pair serves as a source and the other electrode of the pair serves as a sink for the power received from the generator 110. Therefore, one electrode is disposed at the opposite voltage (pole) to the other so that power from the generator is drawn directly from one electrode to the other. The bipolar electrode arrangement insures more localized and smaller heat ablation volumes, but the embodiment is not so limited.

The alternating polarity series of energy directors includes various series combinations of alternating polarities. For example, in an embodiment using six (6) energy directors, the alternating polarity is: positive polarity (+), negative polarity (−), +, −, +, −. An alternative polarity series is: +, +, −, −, +, +. Another alternative polarity series is: −, −, +, +, −, −. Yet another alternative polarity series is: +, +, +, −, −, −. Still other alternative polarity series can include: +, +, −, +, −, −. These examples are exemplary only, and the tissue ablation system 100 described herein is not limited to six (6) electrodes or to these alternating polarities.

The energy directors 104, while configured appropriately for insertion into particular tissue types, have a shape and a pattern that supports coupling to the target tissue and allows the energy directors 104 to deliver sufficient energy to cause the tissue to become hemostatic, such as by coagulation of the tissue, thereby facilitating resection of a selected tissue volume. The energy directors 104 of an embodiment include rigid shafts that are of sufficient stiffness to be easily urged into the target tissue 199 and coupled to the tissue 199 while retaining their shape.

The energy directors 104 terminate in non- or minimally-traumatic tissue-penetrating tips of various configurations known in the art as appropriate to the tissue type of the target tissue 199. The energy director tip configurations of an embodiment include fully rounded tips, flat tips, blunt tips, and rounded tips, but are not so limited. These configurations facilitate insertion of the energy directors into different types of target tissue while protecting the user from sharp points that, during normal handling, pose a puncture hazard to the user. This is particularly important since the energy directors could be contaminated with potentially deadly material including viruses such as Hepatitis-C and Human Immunodeficiency Virus (HIV) that could be transmitted to the user through a puncture wound.

The energy directors of an embodiment can have many different sizes depending upon the energy delivery parameters (current, impedance, etc.) of the corresponding system. For example, energy director diameters are approximately in the range of 0.015 inches to 0.125 inches, but are not so limited. Energy director lengths are approximately in the range of 4 cm to 10 cm, but are not so limited. Energy directors include materials selected from among conductive or plated plastics, super alloys including shape memory alloys, and stainless steel, to name a few.

The energy directors 104 of various alternative embodiments can include materials that support bending and/or shaping of the energy directors 104. Further, the energy directors 104 of alternative embodiments can include non-conducting materials, coatings, and/or coverings in various segments and/or proportions along the shaft of the energy director 104 as appropriate to the energy delivery requirements of the corresponding procedure and/or the type of target tissue.

The generator 110 of an embodiment delivers prespecified amounts of energy at selectable frequencies in order to coagulate and/or cut tissue, but is not so limited. The generator 110 of an embodiment is an RF generator that supports output power in the range of approximately zero to 200 Watts, output current in the range of approximately 0.1 amps to four (4) amps, and output impedances generally in the range of approximately two (2) to 150 Ohms, across a frequency range of approximately 1 kHz to 1 MHz, but is not so limited.

It is understood that variations in the choice of electrical output parameters from the generator to monitor or control the tissue ablation process may vary widely depending on operator experience, technique, and/or preference. For example, in one embodiment a common voltage is applied to all the energy directors of an array simultaneously. As an alternative embodiment, the operator may choose to control the current to the individual energy directors of the array or the total current of the array as a whole.

Further, voltage variations on each energy director can be applied to achieve constant current output from each energy director. Alternatively, constant power output from each energy director may be sought in some procedures. Additionally, voltage variations or phase differences between energy directors can be implemented to achieve prespecified temperature distributions in the tissue as monitored by temperature sensors in the tissue or by visualization of temperature distribution using techniques known in the art. Accordingly, the choice of electrical output type, sequence, and levels and the distribution to the energy directors of the array should be considered to have wide variations within the scope of this invention.

The tissue ablation system 100 can include any number of additional components like, for example, a controller 120 to semi-automatically or automatically control delivery of energy from the generator. The controller can, for example, increase the power output to the electrodes, control temperature when the energy directors include temperature sensors or when receiving temperature information from remote sensors, and/or monitor or control impedance, power, current, voltage, and/or other output parameters. The functions of the controller 120 can be integrated with those of the generator 110, can be integrated with other components of the tissue ablation system 100, or can be in the form of stand-alone units coupled among components of the tissue ablation system 100, but are not so limited.

Moreover, the tissue ablation system 100 can include a display 130 that provides a display of heating parameters such as temperature for one or more of the energy directors, impedance, power, current, timing information, and/or voltage of the generator output. The functions of the display 130 can be integrated with those of the generator 110, can be integrated with other components of the tissue ablation system 100, or can be in the form of stand-alone units coupled among components of the tissue ablation system 100, but are not so limited.

Various alternative embodiments of the tissue ablation system 200 can also include a biocompatible thermal shield 140. The thermal shield 140 serves to protect the organs and tissue that surround the target biological tissue 199 from the effects of the procedures described herein associated with treatment using the tissue ablation system 200.

Placement of the energy directors described herein controls the distribution of energy imparted to the target tissue. As such, the energy director configurations described herein support approximately uniform energy distribution and/or current density, and thus more uniform temperatures, through the target tissue volume. An example of this includes the use of RF energy where, for a number of energy directors, and as described below, generally uniform energy distribution is obtained using relatively smaller spacing between the energy directors toward the outside of a linear energy director array and relatively larger spacing between the energy directors toward the center of the energy director array. The spacing between the energy directors is established and maintained using the energy director guide, a description of which follows.

Figure 2:
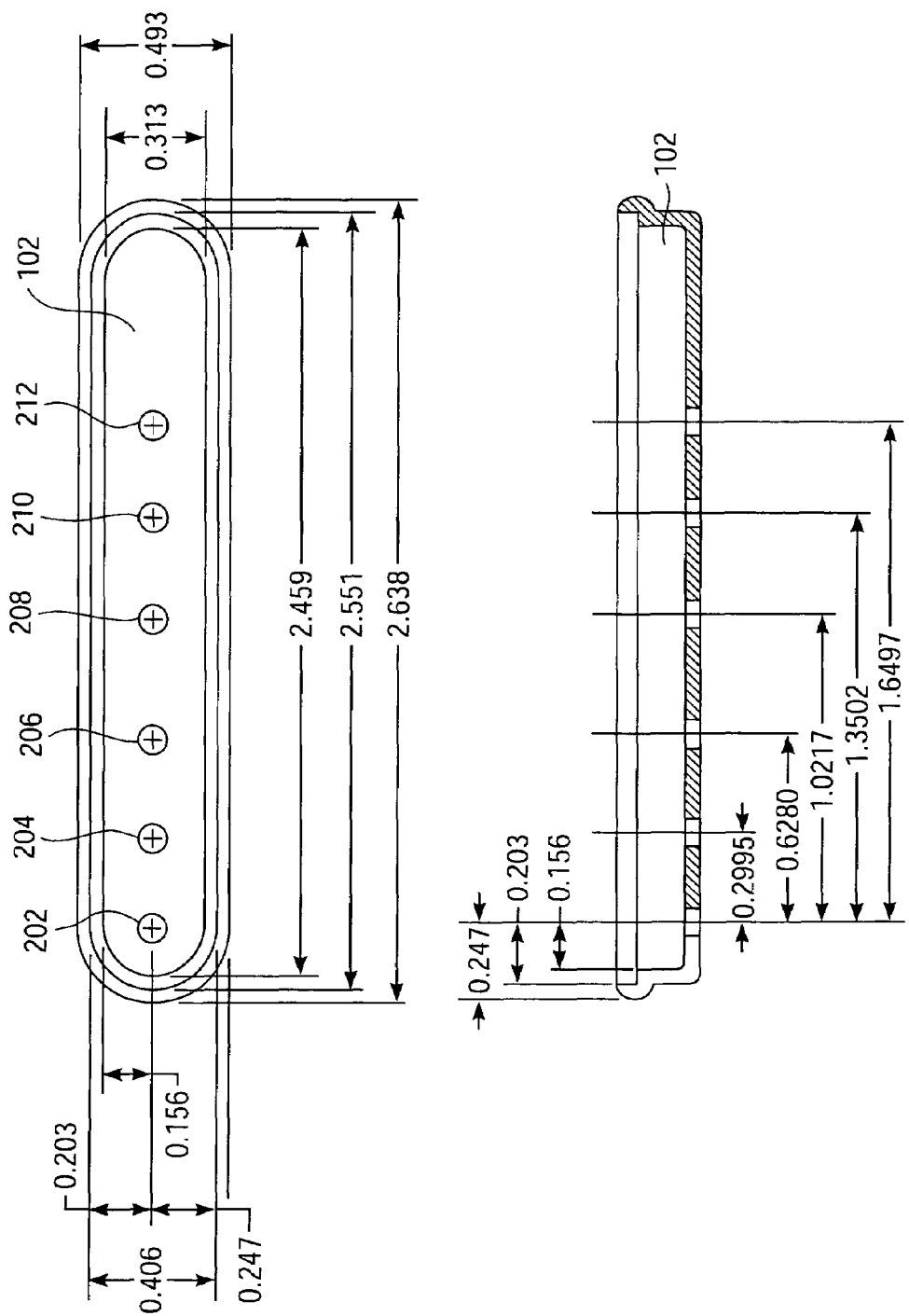
FIG. 2 and FIG. 3 are schematics of the energy director guide, including various views, under an embodiment.
Figure 3:
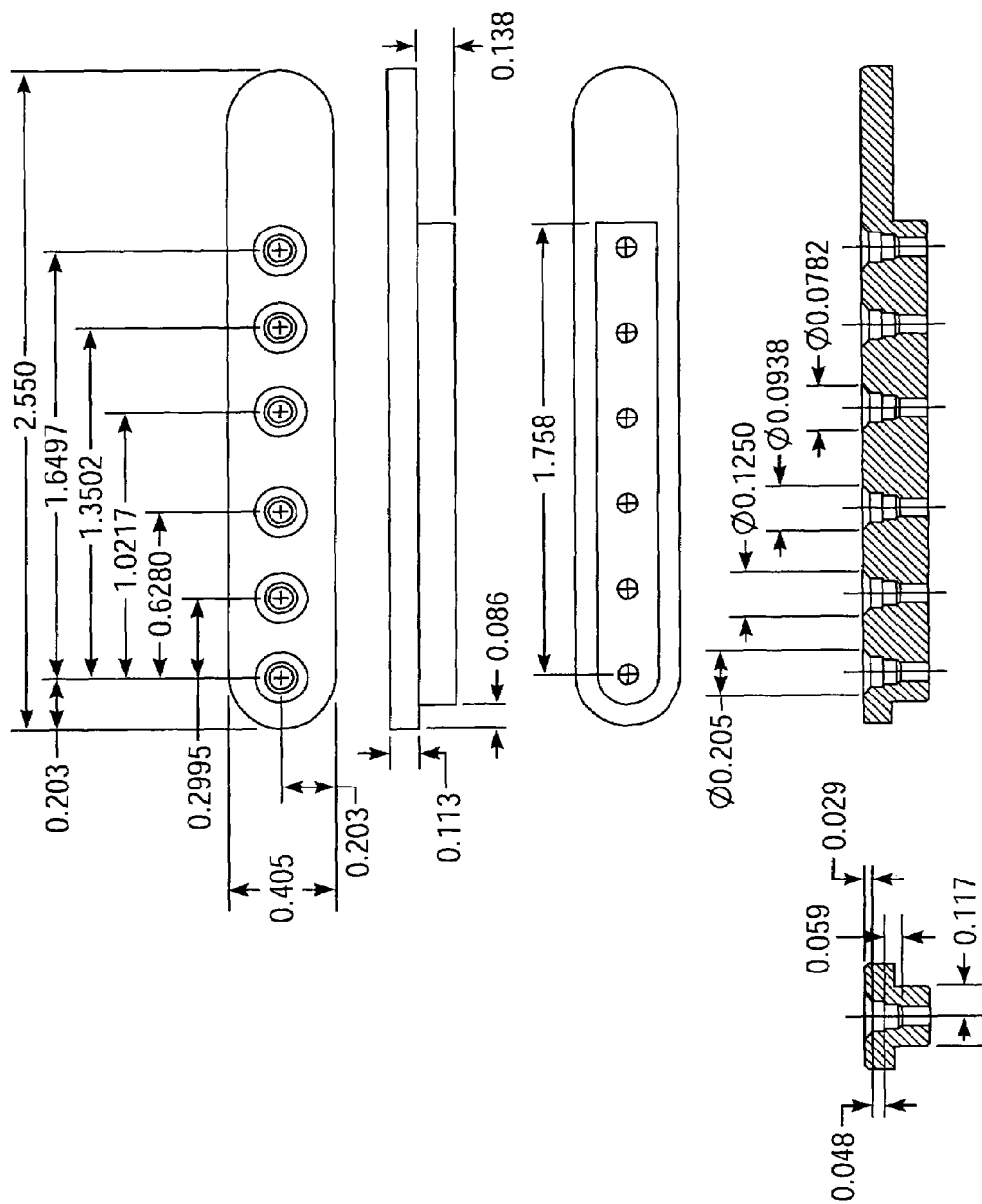

FIGS. 2 and 3 are schematics of an energy director guide 102, including various views, under an embodiment. The dimensions shown are in inches. The energy director guide 102 includes a support body having a linear series of channels 202–212 that receive or carry the energy directors. The support body of an embodiment includes first and second end portions with a surface extending between the first and second end portions. The channels 202–212 can also be referred to as orifices or openings, but are not so limited. The energy director guide of various alternative embodiments can include a non-linear series of channels, and various combinations of a linear and a non-linear series of channels. The energy directors of an embodiment alternate in polarity or, alternatively, are in groups or sets that alternate in polarity, as described above, but the embodiment is not so limited. The configuration of the channels 202–212 in the guide supports delivery of an energy distribution or radiation pattern in the tissue by the energy directors that provides sufficient and even coagulation in the target tissue volume. Typically an ablation width in the range of approximately 0.5 cm to 1.5 cm is used to facilitate the resection, but the embodiment is not so limited. The energy director guides include biocompatible materials like, for example, non-conductive plastics like polycarbonate plastic, ULTEM® (polyetherimide), and Acrylonitrile Butadiene Styrene (ABS) plastic, but are not so limited.

While six (6) channels are shown for illustrative purposes, alternative embodiments can include differing numbers of channels. The spacing among the channels 202–212 varies according to the total number of energy directors received in the energy director guide 102, as described further below. Generally, to account for electromagnetic coupling among the energy directors when the energy directors are coupled to the generator, the relative spacing among the center-most channels (206 and 208 in this embodiment) is largest while relative spacing among the end-most channels (202/204 and 210/212 in this embodiment) is smallest.

As described above, uniform energy distribution is important when generating an avascular volume of tissue suitable for bloodless or near-bloodless resection. The energy director guide 102 described herein provides uniform energy distribution via the energy directors using a channel spacing, and consequently an energy director configuration, that accounts for electromagnetic coupling effects among neighboring energy directors. The energy director guide 102 of an embodiment includes six (6) channels 202–212 that, in operation, receive three (3) pairs of bipolar energy directors. The spacing between channels 202 and 204 is approximately 0.2995 inches. The spacing between channels 204 and 206 is approximately 0.3285 inches. The spacing between channels 206 and 208 is approximately 0.3937 inches. The spacing between channels 208 and 210 is approximately 0.3285 inches. The spacing between channels 210 and 212 is approximately 0.2995 inches.

Figures 4A, 4B:
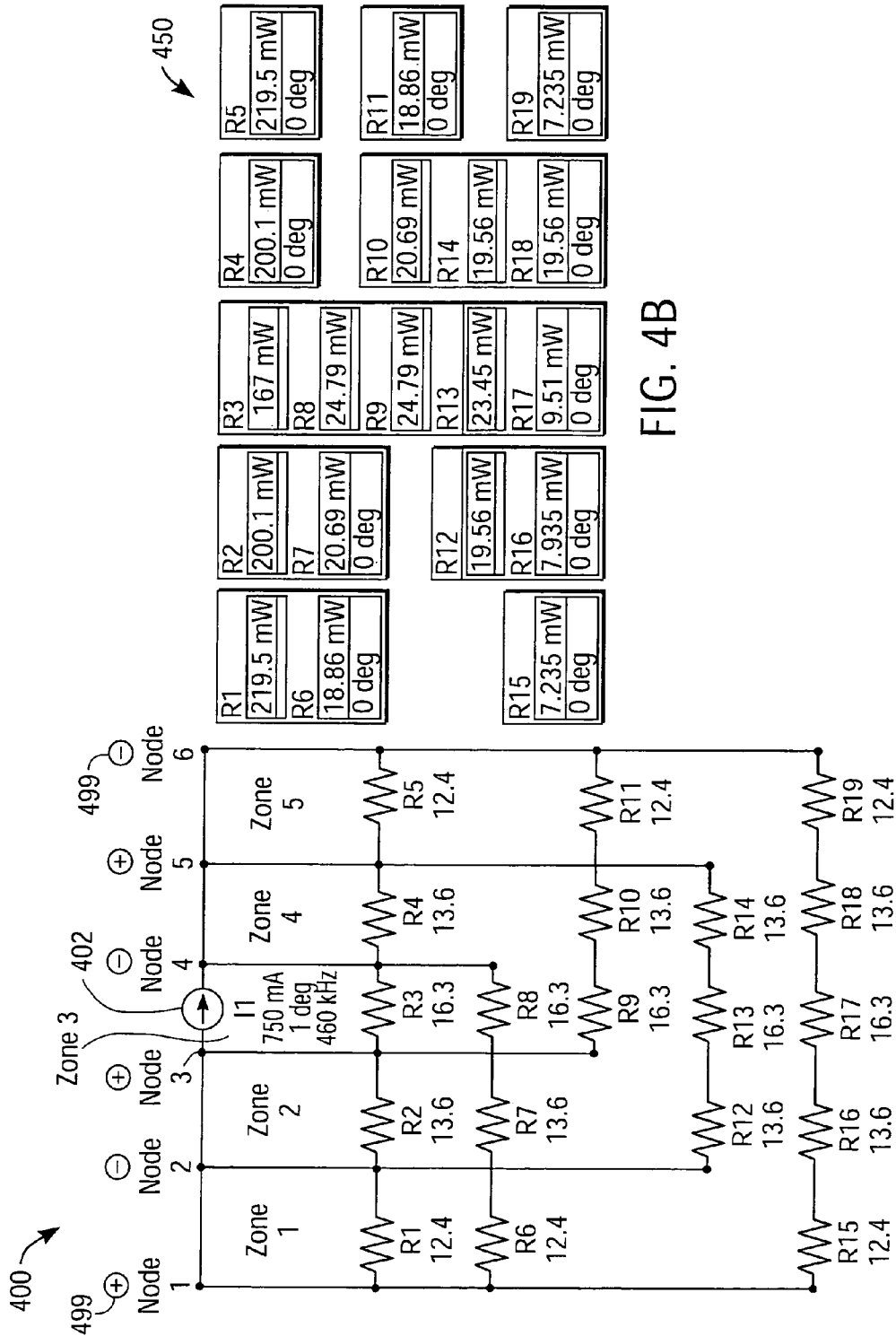
FIG. 4A shows a resistive network model for an energy director configuration including six (6) energy directors, under the embodiment of FIGS. 2 and 3.
FIG. 4B shows a table including power dissipation values corresponding to an energy director configuration providing balanced energy, under the embodiment of FIG. 4A.

The guide channel spacing that provides relatively uniform energy distribution is generated using resistive network models, but is not so limited. FIG. 4A shows a resistive network model 400 for an energy director configuration including six (6) bipolar energy directors, under the embodiment of FIGS. 2 and 3. Each of the six bipolar energy directors is represented by one of nodes 1–6, wherein each node is assigned an alternating polarity 499, but the polarity assigned in this example is not limiting. The model 400 includes a number of resistors R1–R19 coupled in various configurations among nodes 1–6 and current source 402, as described further below. The current source 402 is arbitrarily selected to produce 750 milliamps (mA) of current, but the model is not so limited.

Generally, the resistor configurations of the model 400 simulate the relative power dissipation, including the coupling effects among the various combinations of alternating polarity nodes, in the tissue volumes ("zones") between the energy directors (nodes), as further described below. Given that biological tissue has a resistivity (resistance per unit volume) that is proportional to the spacing between energy directors, the resistor values of the model are iteratively varied to represent different channel spacing.

With reference to FIG. 4A, resistor RI models the power dissipation in zone 1 as a result of current flowing between nodes 1 and 2. Likewise, resistors R2, R3, R4, and R5 each model the power dissipation as a result of current flowing between the nodes that define each of zones 2–5, respectively. The series combination of resistors R6, R7, and R8 couple between nodes 1 and 4 and model the power dissipation across zones 1, 2, and 3 as a result of the current flowing between nodes 1 and 4. The series combination of resistors R9, R10, and R11 couple between nodes 3 and 6 and model the power dissipation across zones 3, 4, and 5 as a result of the current flowing between these nodes. The series combination of resistors R12, R13, and R14 couple between nodes 2 and 5 and model the power dissipation across zones 2, 3, and 4 as a result of the current flowing between nodes 2 and 5. Finally, the series combination of resistors R15, R16, R17, R18, and R19 couple between nodes 1 and 6 and model the power dissipation across zones 1, 2, 3, 4, and 5 as a result of the current flowing between nodes 1 and 6. FIG. 4B shows a table 450 including power dissipation values corresponding to an energy director configuration providing balanced energy, under the embodiment of FIG. 4A.

FIG. 4C is a table 480 including power dissipation and spacing information corresponding to an energy director configuration providing balanced energy, under the embodiment of FIG. 4A. This table 480 includes total power dissipation 482 for each zone of the resistive network model 400. The balanced energy director configuration uses non-uniform channel spacing in the energy director guide to account for the effects of electromagnetic coupling, as described above, under the embodiment of FIG. 2. In determining the total power dissipation per zone 482, the resistor values for the zones of an array are varied iteratively until the total power dissipation per zone 482 is approximately equal; the spacing per zone is proportional to the resistor values. The total power dissipation across zones 1–5 in a balanced energy director configuration is approximately 246 milliwatts (mW), 248 mW, 250 mW, 248 mW, and 246 mW, respectively, but is not so limited. Consequently, the power dissipation or distribution across the zones is approximately uniform.

Using the final values for the total power dissipation per zone 482, spacing ratios per zone 484 and 486 are generated. In an embodiment, two different spacing ratios per zone 484 and 486 are generated, but the embodiment is not so limited. A first spacing ratio per zone 484 references the spacing of the zones to the proximal-most/distal-most zones (zones 1 and 5) of the array, and a second spacing ratio per zone 486 references the spacing of the zones to the center zone (zone 3) of the array. Note, however, that the spacing ratios per zone can be referenced to any zone of the array in alternative embodiments.

Using either of the spacing ratios per zone 484 and 486, the relative spacing among the channels is determined by assigning a reference spacing value to the reference zone (the zone for which the spacing ration is one (1)). The spacing values for all other zones of the array are then each determined using the spacing ratio for each associated zone as a multiplier against the reference spacing value. Reference spacing values are selected using techniques known in the art, wherein the largest spacing value between the energy directors of an array is approximately in the range of 0.75 cm to 2.00 cm, but the embodiment is not so limited.

Alternative embodiments of the tissue ablation system include differing numbers of energy directors and, therefore, differing numbers of channels in the energy director guide. For example, one alternative embodiment includes an energy director guide having a series of eight (8) channels that receive energy directors of alternating polarity. As described above, the channel spacing in this alternative embodiment is also determined using a resistive network model simulation, but is not so limited.

Figure 5A:
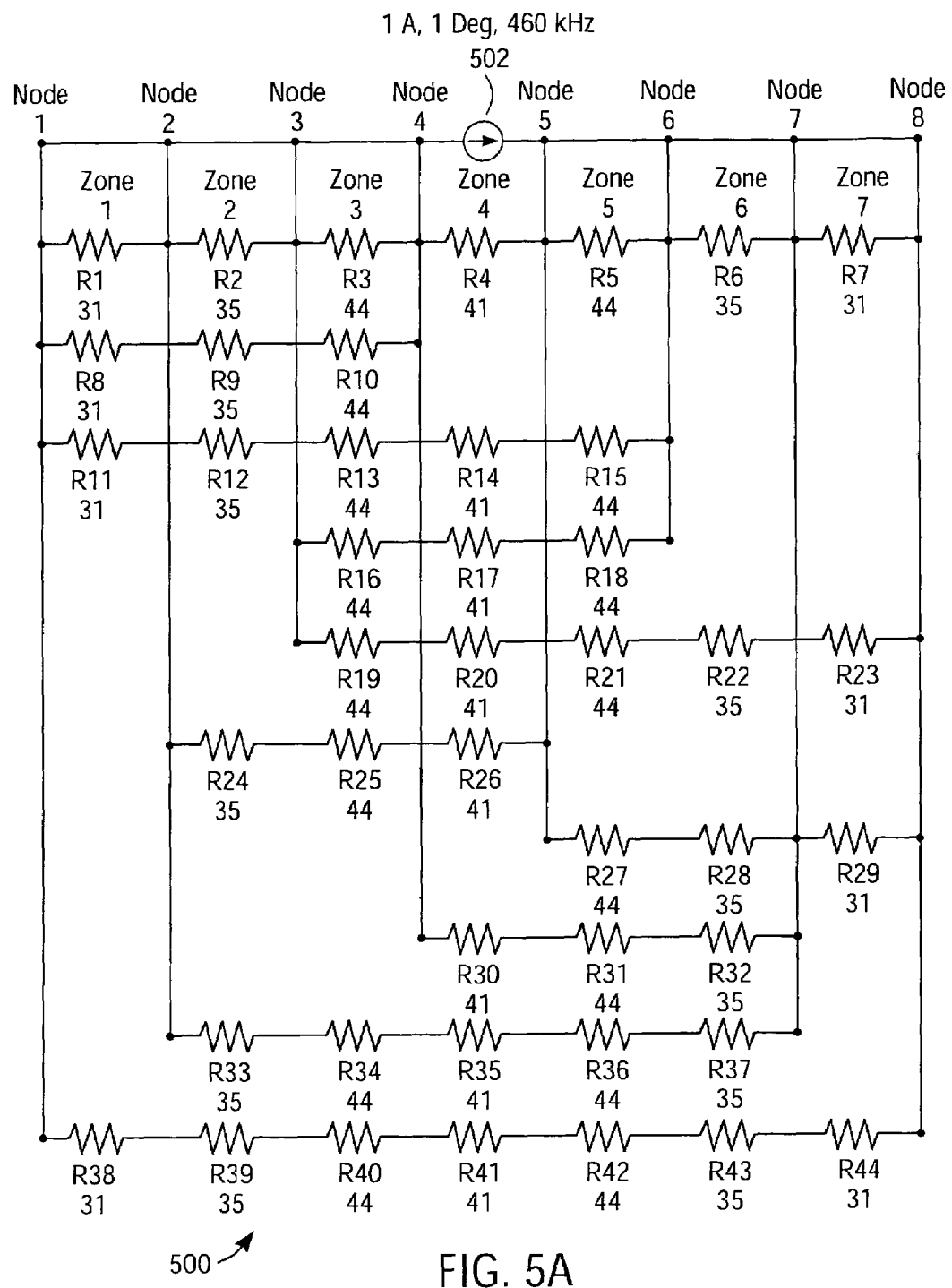
FIG. 5A shows a resistive network model for an energy director configuration including eight (8) energy directors, under an alternative embodiment.

FIG. 5A shows a resistive network model 500 for an energy director configuration including eight (8) bipolar energy directors, under an alternative embodiment. Extrapolating from the embodiment of FIG. 2, the energy director guide of this example includes eight (8) channels, each of which receive an energy director. Each of the eight bipolar energy directors is represented by one of nodes 1–8, wherein each node is assigned an alternating polarity. The model 500 includes a number of resistors R1–R44 coupled in various configurations among nodes 1–8 and current source 502, as described further below. The current source 502 is arbitrarily selected to produce one (1) amp of current, but the model is not so limited.

Referring to FIG. 5A, resistor RI models the power dissipation as a result of current flowing between nodes 1 and 2. Likewise, resistors R2, R3, R4, R5, R6, and R7 each model the power dissipation as a result of current flowing between the nodes that define each of zones 2–7, respectively. The series combination of resistors R8, R9, and R10 couple between nodes 1 and 4 and model the power dissipation across zones 1, 2, and 3 as a result of the current flowing between nodes 1 and 4. The series combination of resistors R11, R12, R13, R14, and R15 couple between nodes 1 and 6 and model the power dissipation across zones 1, 2, 3, 4, and 5 as a result of the current flowing between nodes 1 and 6.

Continuing, the series combination of resistors R16, R17, and R18 couple between nodes 3 and 6 and model the power dissipation across zones 3, 4, and 5 as a result of the current flowing between nodes 3 and 6. The series combination of resistors R19, R20, R21, 22, and R23 couple between nodes 3 and 8 and model the power dissipation across zones 3, 4, 5, 6, and 7 as a result of the current flowing between nodes 3 and 8. The series combination of resistors R24, R25, and R26 couple between nodes 2 and 5 and model the power dissipation across zones 2, 3, and 4 as a result of the current flowing between nodes 2 and 5. The series combination of resistors R27, R28, and R29 couple between nodes 5 and 8 and model the power dissipation across zones 5, 6, and 7 as a result of the current flowing between nodes 5 and 8.

Figure 5B:
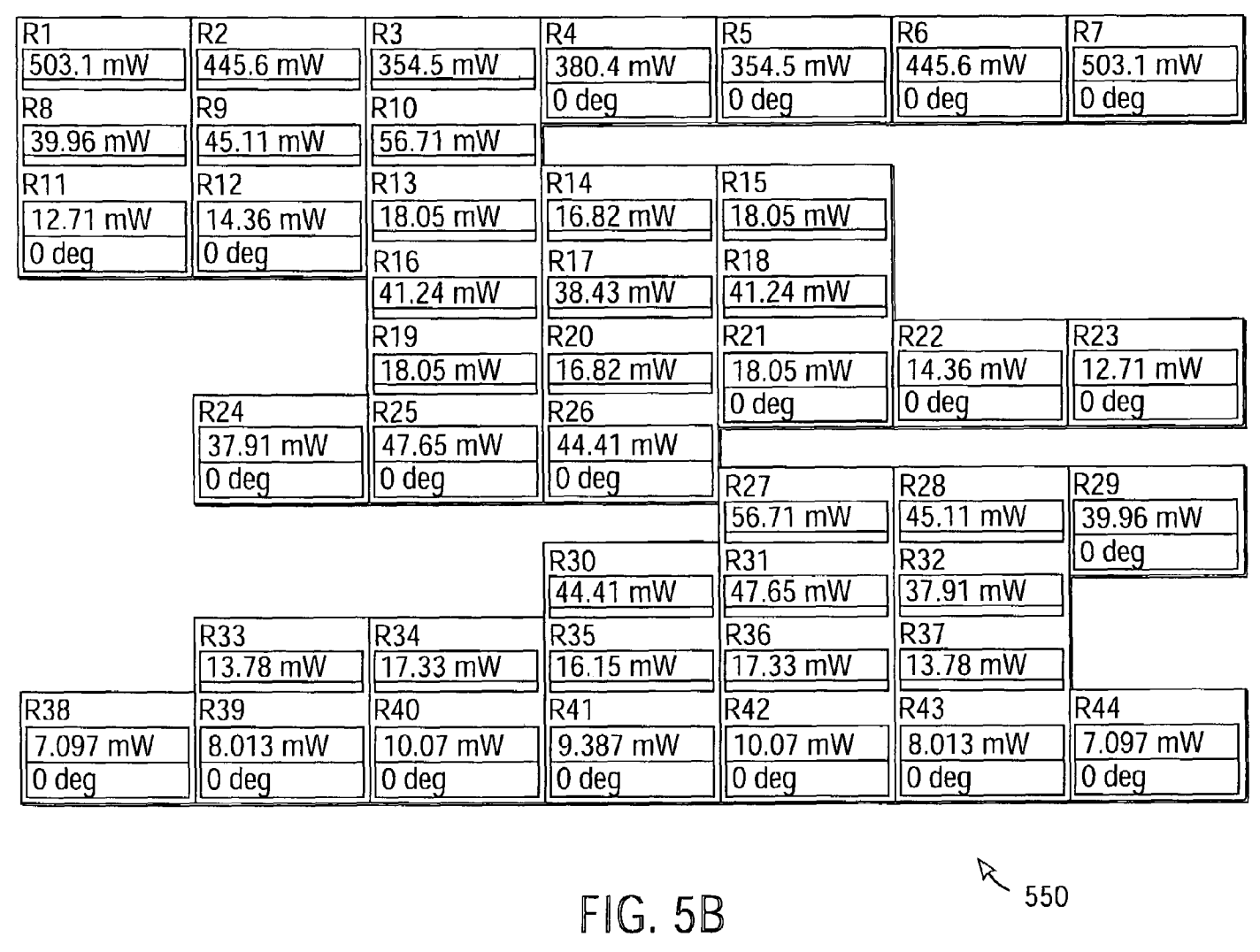

Further, the series combination of resistors R30, R31, and R32 couple between nodes 4 and 7 and model the power dissipation across zones 4, 5, and 6 as a result of the current flowing between nodes 4 and 7. The series combination of resistors R33, R34, R35, R36, and R37 couple between nodes 2 and 7 and model the power dissipation across zones 2, 3, 4, 5, and 6 as a result of the current flowing between nodes 2 and 7. Finally, the series combination of resistors R38, R39, R40, R41, R42, R43, and R44 couple between nodes 1 and 8 and model the power dissipation across zones 1, 2, 3, 4, 5, 6, and 7 as a result of the current flowing between nodes 1 and 8. FIG. 5B shows a table 550 including power dissipation values corresponding to an energy director configuration providing balanced energy, under the embodiment of FIG. 5A.

FIG. 5C is a table 580 including power dissipation information 582 and spacing information 584 and 586 corresponding to an energy director configuration providing balanced energy, under the embodiment of FIG. 5A. This power dissipation table 580 includes total power dissipation 582 for each zone of the resistive network model 500. The balanced energy director configuration uses non-uniform channel spacing in the energy director guide to account for the effects of electromagnetic coupling, as described above. The total power dissipation across zones 1–7 is approximately 563 mW, 565 mW, 564 mW, 567 mW, 564 mW, 565 mW, and 563 mW, respectively. Consequently, the power dissipation or distribution across the zones is approximately uniform.

The embodiments described above with reference to FIGS. 2, 3, 4, and 5 provide approximately uniform power distribution among the tissue zones of a target tissue volume. However, as power is proportional to the product of voltage and current, alternative embodiments of the energy director array are configured to provide approximately uniform current density through the target tissue volume. As such, the tissue ablation systems of various alternative embodiments generate avascular volumes of coagulated tissue using approximately uniform current,density. The energy director guide channel spacing that provides uniform current density is determined using resistive network models, as above, but is not so limited.

Figures 6A, 6B:
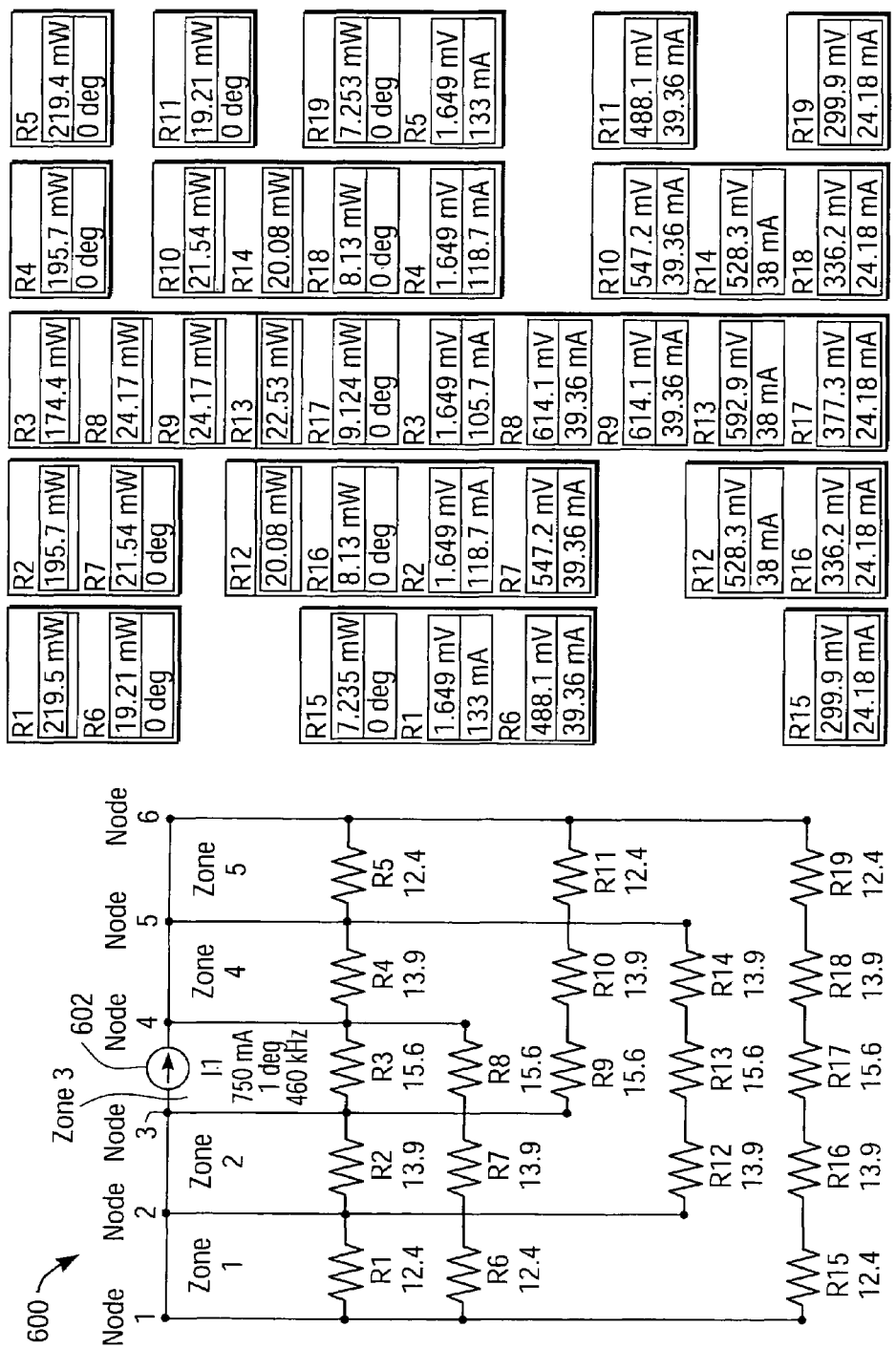
FIG. 6A shows a resistive network model for an energy director configuration including six (6) energy directors (five zones), under an alternative embodiment.
FIG. 6B shows a table including power dissipation information corresponding to an energy director configuration providing balanced energy, under the embodiment of FIG. 6A.

The guide channel spacing that provides relatively uniform current density is generated using resistive network models, but is not so limited. FIG. 6A shows a resistive network model 600 for an energy director configuration including six (6) bipolar energy directors, under an alternative embodiment of FIGS. 2 and 3. Each of the six bipolar energy directors is represented by one of nodes 1–6, wherein each node is assigned an alternating polarity. The model 600 includes a number of resistors R1–R19 coupled in various configurations among nodes 1–6 and current source 602, as described above with reference to FIG. 4A. The relative power dissipation among the different zones is proportional to the current density in the associated tissue zones. The current source 602 is arbitrarily selected to produce 750 milliamps (mA) of current, but the model is not so limited. FIG. 6B shows a table 650 including power dissipation information corresponding to an energy director configuration providing balanced energy, under the embodiment of FIG. 6A.

FIG. 6C is a table 680 including current density and spacing information corresponding to an energy director configuration that provides balanced energy, under the embodiment of FIG. 6A. This table 680 includes the current density per zone 682 for the zones of the resistive network model 600. The balanced energy director configuration uses non-uniform channel spacing in the energy director guide to account for the effects of electromagnetic coupling, as described above. In determining the current density per zone 682, the resistor values for the zones of an array are varied iteratively until the current density per zone 682 is approximately equal; the channel spacing information is proportional to and derived from the final resistor values that provide approximately uniform current density. The current density per zone across zones 1–5 is approximately 15.85 milliamps (mA)/spacing value, 15.8446 mA/spacing value, 15.80769 mA/spacing value, 15.8446 mA/spacing value, and 15.85 mA/spacing value, respectively, but is not so limited. Consequently, the current density across the zones is approximately uniform.

Using the current density per zone 682, spacing ratios per zone 684 and 686 are generated. In an embodiment, two different spacing ratios per zone 684 and 686 are generated, but the embodiment is not so limited. A first spacing ratio per zone 684 references the spacing of the zones to the proximal-most/distal-most zones (zones 1 and 5) of the array, and a second spacing ratio per zone 686 references the spacing of the zones to the center zone (zone 3) of the array. Note, however, that the spacing ratios per zone can be referenced to any zone of the array in alternative embodiments.

Using either of the spacing ratios per zone 684 and 686, the relative spacing among the channels is determined by assigning a reference spacing value to the reference zone (the zone for which the spacing ration is one (1)). The spacing values for all other zones of the array are then each determined using the spacing ratio for each associated zone as a multiplier against the reference spacing value. Reference spacing values are selected using techniques known in the art.

Alternative embodiments of the tissue ablation system include differing numbers of energy directors and, therefore, differing numbers of channels in the energy director guide. As described above, the channel spacing in these alternative embodiments is also determined using a resistive network model simulation, but is not so limited.

The energy director guide of an alternative embodiment is reconfigurable to support a number of energy director configurations. For example, the energy director guide can include channels that are moveable between a number of prespecified locations in the energy director guide so that placement of the channels in a first set of prespecified locations along the guide supports the six energy guide configuration described above, and placement of the channels in a second set of prespecified locations along the guide supports the eight energy guide configuration described above. Using this embodiment, a user can support many different energy director configurations with a single energy director guide.

Referring again to FIG. 1, the energy director guide of an embodiment independently couples each of the energy directors to the generator via the energy director guide. Further, the energy director guide independently secures a position of each of the energy directors in the target tissue.

Figure 7:
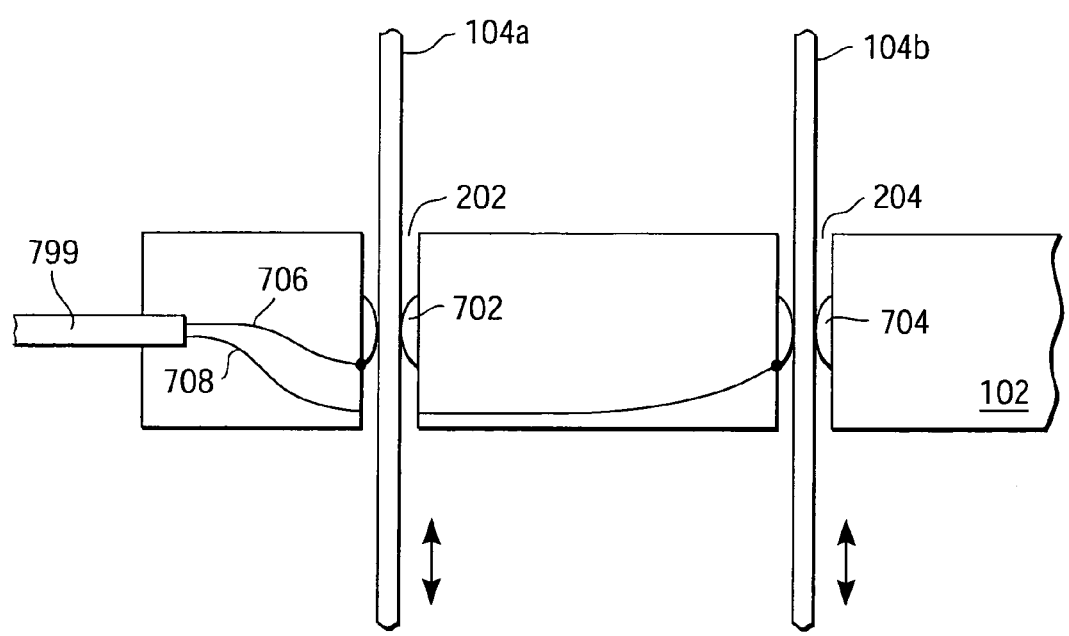
FIG. 7 is a side view of an energy director guide using direct coupling, under an embodiment.

Regarding electrical coupling of the energy directors to the generator, the energy director guide of an embodiment uses direct electrical coupling, while alternative embodiments use indirect electrical coupling. FIG. 7 is a side view of an energy director guide 102 using direct coupling, under an embodiment. Each channel 202 and 204 of the guide 102 includes one or more contacts 702 and 704 that couple conductors 706 and 708 of an energy conduit 799 from the generator (not shown) directly to the corresponding energy director 104a and 104b. When using bipolar energy directors, for example, a first conductor 706 carrying signals of a first polarity couples to a first energy director 104a via a first contact 702. Likewise, a second conductor 708 carrying signals of a second polarity couples to a second energy director 104b via a second contact 704. The contacts of an embodiment are fabricated from materials with good spring and wear properties including, for example, stainless steel and beryllium copper. Furthermore, the contacts of alternative embodiments can also secure or assist in securing a position of the energy directors, but are not so limited.

Figure 8:
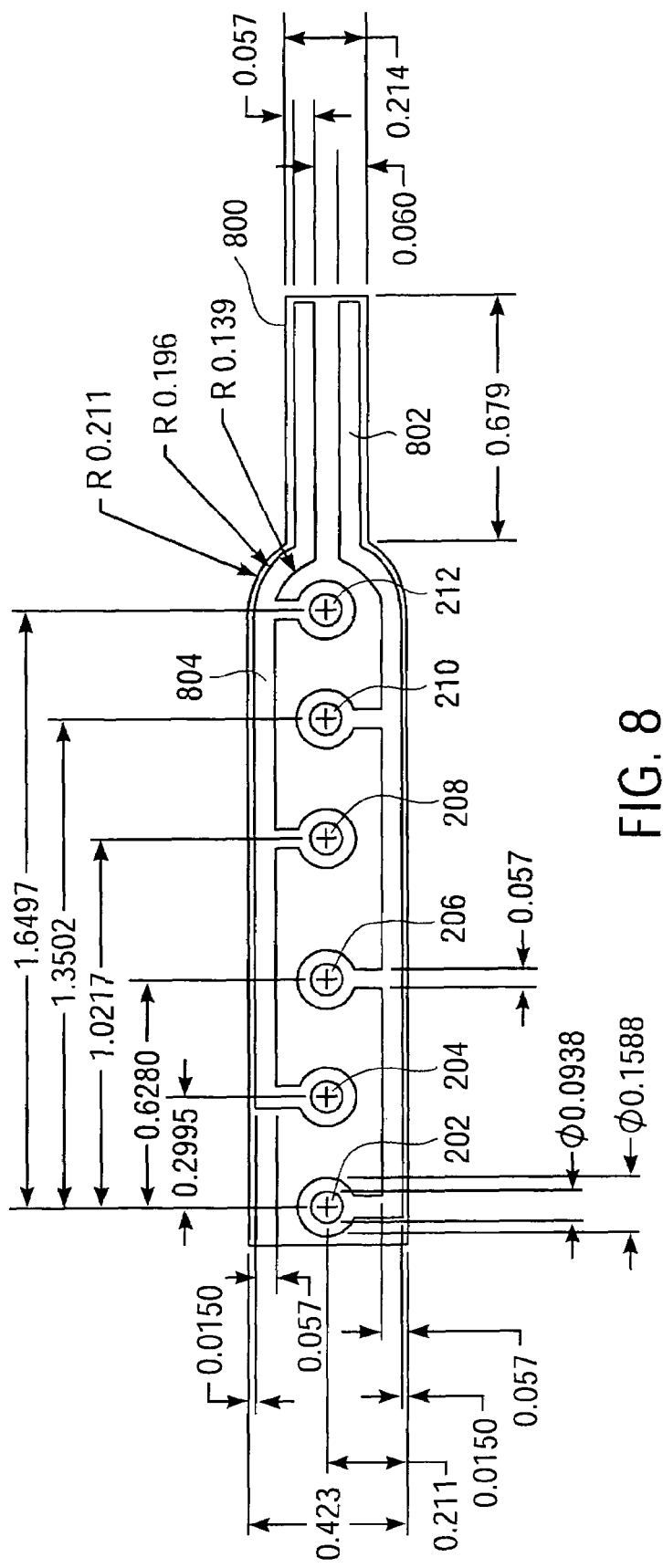
FIG. 8 is a schematic of a circuit board for use in an energy director guide, under the embodiment of FIG. 2.

FIG. 8 is a schematic of a circuit board 800 for use in an energy director guide, under the embodiment of FIG. 2. The circuit board 800 directly couples power signals having the appropriate polarity from a power source to the corresponding channels, and thus the corresponding energy directors, via conducting traces 802 and 804. In the circuit board 800 of an embodiment using alternating polarities, a first conducting trace 802 carries an electrical signal having a first polarity, for example a positive polarity, among the energy directors of channels 202, 206, and 210. A second conducting trace 804 carries an electrical signal having a second polarity, for example a negative polarity, among the energy directors of channels 204, 208, and 212, but the embodiment is not so limited.

Figure 9:
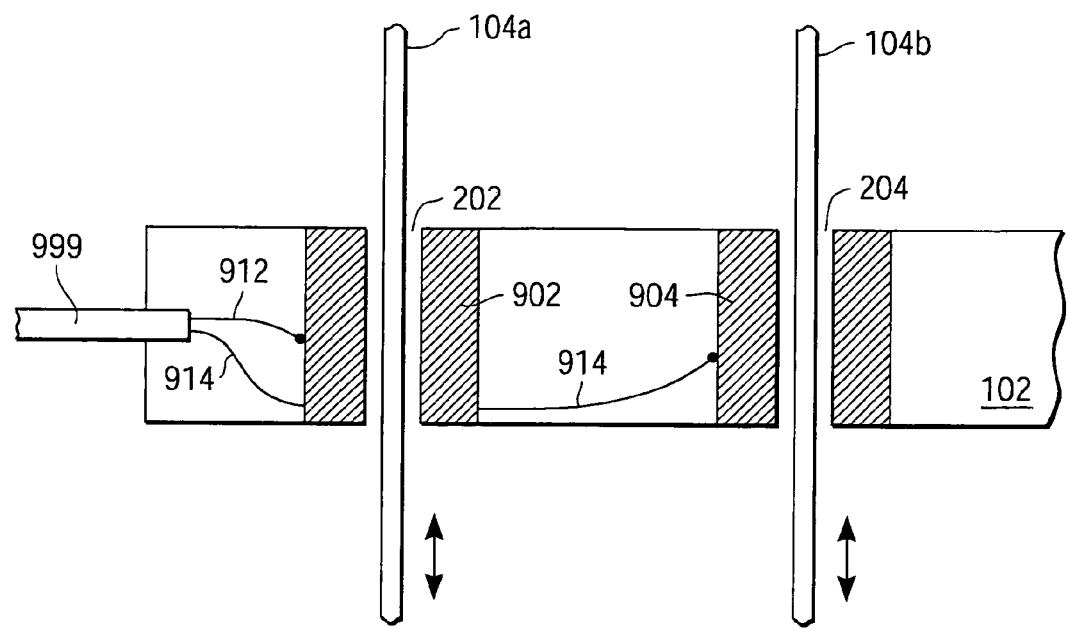
FIG. 9 is a side view of an energy director guide using indirect coupling, under an embodiment.

In an embodiment using indirect coupling, a coil of electrically conductive material that is insulated along its length is wound such that it forms a magnetic field around the electrically conductive energy director thereby inducing a current flow in the energy director. FIG. 9 is a side view of a guide 102 using indirect coupling, under an embodiment. Each channel 202 and 204 of the guide 102 includes a coil or winding of conductive material 902 and 904 that indirectly couples conductors 912 and 914 of an energy conduit 999 from the power source (not shown) to the corresponding energy director 104a–104b.

Figure 10:
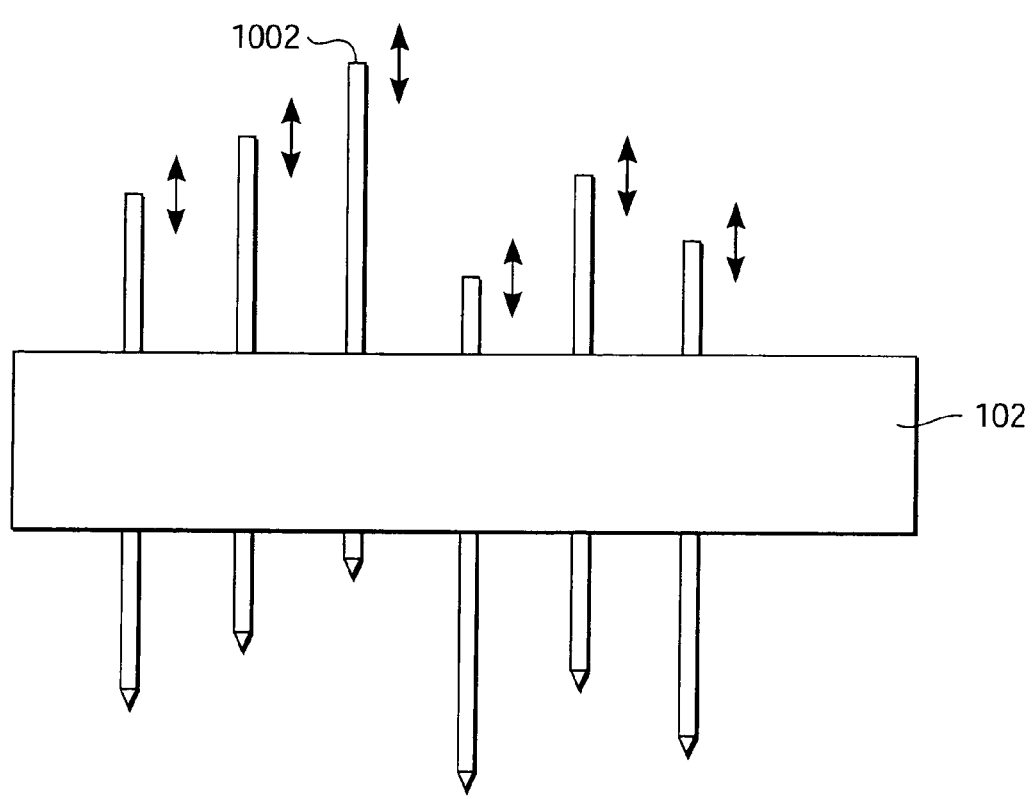
FIG. 10 shows an energy director guide that provides for independent control of the insertion depth of each energy director, under an embodiment.

As described above, the energy director guide of an embodiment supports independent control of the position of the corresponding energy directors. FIG. 10 shows a guide 102 that provides for independent control of the insertion depth of each energy director 1002, under an embodiment. The guide 102 provides independent control of the insertion of each energy director 1002 to independently variable depths within the target tissue. The insertion of the energy directors 1002 can be performed individually or simultaneously as appropriate to the procedure. As such, each energy director 1002 can be inserted into the target tissue to a different depth, thereby allowing the physician or clinician to avoid critical anatomical structures with the application of RF energy. This is particularly valuable since there often are present critical anatomical structures into which an energy director 1002 should not be inserted. Further, independent control of insertion depth for each energy director 1002 supports the use of various visualization methods such as ultrasound stenography, Computerized Tomography (CT), and Magnetic Resonance Imaging (MRI) in placement of the energy directors 1002 in target tissue.

Once inserted into the target tissue, components of the energy director guide exert enough force on the corresponding energy directors to secure them in the target tissue so that natural body movement will not push the energy directors out. The components of the energy director guide exert a force on the energy directors approximately in the range of 0.5 newton to 5 newton, but are not so limited.

Figure 11:
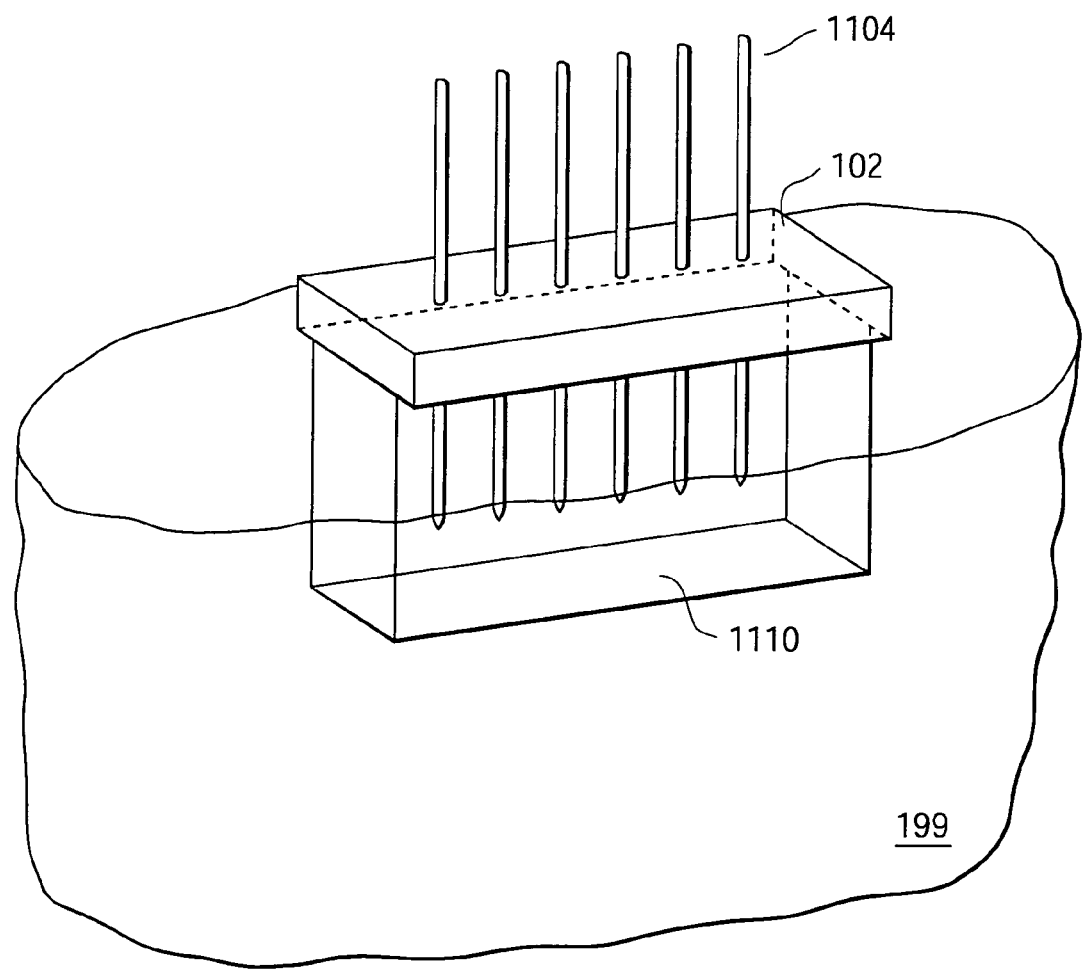
FIG. 11 and FIG. 12 show operation of the tissue ablation system to generate an avascular volume of tissue, under the embodiment of FIG. 2.

FIG. 11 shows operation of the tissue ablation system to generate an avascular volume of tissue, under the embodiment of FIG. 2. Generally, the ablation procedure begins by positioning the energy directors 1104 at a first depth in the target tissue 199. The depth shown is exemplary only, and is not a limiting depth. As such, the first depth at which the energy directors 1104 are placed is not limited to a particular depth except by the length of the energy directors 1104 used in a particular procedure or the anatomical structures present in the target tissue. Following placement of the energy directors, the user applies power to the positioned energy directors 1104, thereby ablating the corresponding volume 1110 of engaged target tissue.

Figure 12:
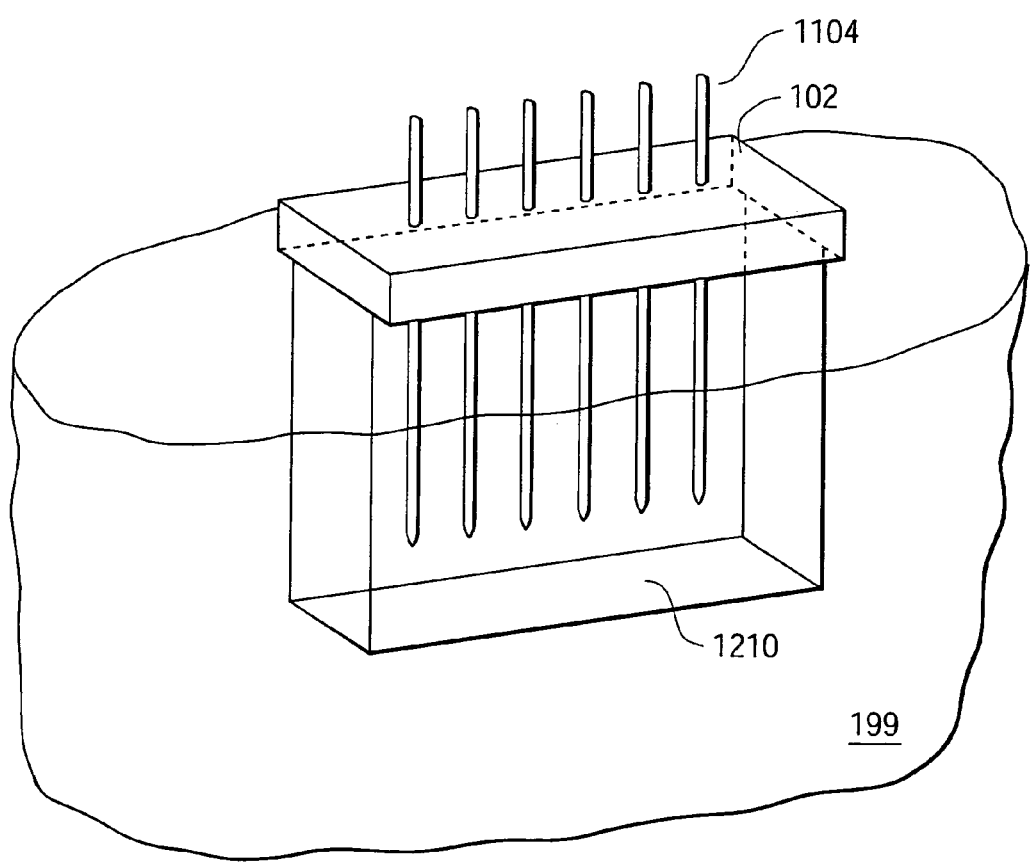

As another example in operation, the tissue ablation system can be used to incrementally ablate a volume of target tissue as the energy directors 1104 are incrementally advanced into the target tissue. FIG. 12 shows operation of the tissue ablation system to generate an avascular volume of tissue, under an alternative embodiment of FIG. 11. Referring to FIG. 12, and following ablation of the tissue volume 1110 associated with the first depth of the energy directors 1104 (FIG. 11), the energy directors 1104 are further advanced to a second depth in the target tissue 199. Following this advancement, the user couples the power to the energy directors 1104, thereby ablating the corresponding increased volume 1210 of engaged target tissue. Advancement of the energy directors 1104 continues until the entire desired volume of issue is rendered avascular or near-avascular. The shape and size of the ablation volume 1110 and 1210 is controlled by the configuration of the electrode cluster, the geometry of he exposed energy director tips, the amount of power applied, the time duration that the power is applied, and cooling of the electrodes, to name a few.

This method is particularly useful to help control several critical parameters including energy density, thermal load from the surrounding tissue, and the electrical impedance of the tissue. When the energy density is too low the thermal effect cannot be achieved. Likewise, when the thermal load from the surrounding tissue is too large the thermal effect will also not be achieved. Low electrical tissue impedance makes it difficult to heat since the dissipated power is proportional to the tissue impedance. Very low or high impedance will also be difficult for some power supplies to deliver the required energy.

Figure 13:
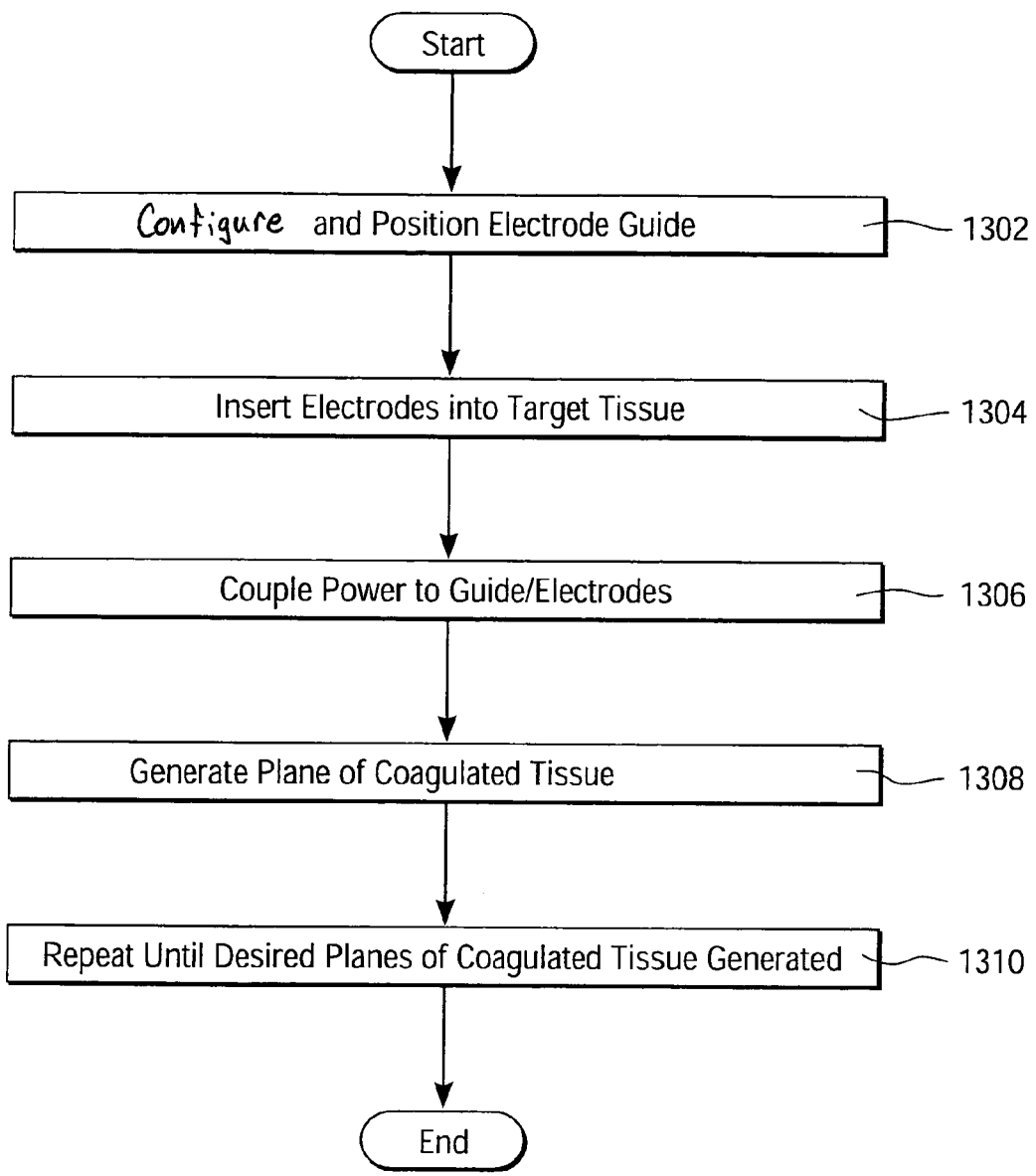
FIG. 13 is a flow diagram for the operation of the tissue ablation system, under the embodiment of FIG. 11 and FIG. 12.

FIG. 13 is a flow diagram for the operation of the tissue ablation system, under the embodiments of FIG. 1, FIG. 11, and FIG. 12. In operation, and depending on the clinical conditions or requirements, a user selects an appropriate configuration of the energy directors, at block 1302. This selection includes, for example, determinations as to the following factors: (i) the number of energy directors in the cluster; (ii) the relative geometry, individual size, and tip exposure of the energy directors; (iii) the geometry of the target tissue region and identification of any tissue regions to be avoided; and (iv) selecting cooled or non cooled electrodes. Further, the selection can include processing image scan data from a CT scan, MRI, ultrasound, and/or other type of scanning device to determine the position of a targeted volume such as a tumor within the patient's body and the desired approach, placement, size, and number of energy directors.

The positioning of the energy directors in an embodiment is preplanned, for example using a workstation, and the heat isotherms and ablation volume and time-course of the ablation are determined. Based on historical or empirical information, the user may determine the desired power to be delivered to the tissue, the temperature as measured by the electrode or measured elsewhere in the tissue by either integrated temperature sensors in the energy directors or satellite temperature-sensing electrodes, the desired time duration of heating, and the characteristics of impedance, to determine energy application timing parameters and control against charring and other undesired effects.

Further, the selection of an embodiment includes sizing of the electrodes based on the target organ. For example, the user can estimate a transverse dimension of the target organ. Using the estimated dimension, the user sizes the electrodes individually or as a group so that the electrodes do not extend beyond the target organ when fully inserted in the target organ.

Following the configuration and planning, the user positions the energy director guide, and inserts the electrodes into the target tissue, at block 1304. The energy directors can be placed individually or in unison within the body tissue, as described herein. Real-time imaging can be used, for example CT, MRI, and/or ultrasound, during placement of the electrodes to determine their proper position within a targeted volume of tissue. The user inserts the energy directors to a desired depth. Additionally, if the energy directors are used with coolant, the user applies the coolant as appropriate.

During some procedures involving the tissue ablation system the user separates the target organ from one or more adjacent organs, but the embodiment is not so limited. This is done to prevent the electrodes from piercing the adjacent organs upon or during insertion into the target organ. Alternatively, the user can place a shield between the target organ and any adjacent organs to protect the adjacent organs from penetration by the electrodes.

The user couples or applies power from the generator to the energy director guide and the energy directors, at block 1306. Alternatively, the power is coupled directly to the energy directors. While power is described in this example, various alternative embodiments can, instead of using power as the controlling parameter, use current, voltage, impedance, temperature, time, and/or any combination of these, to control the tissue ablation process. The power can be coupled to all of the energy directors in unison, or sequentially in a predetermined sequence, as appropriate to the treatment procedure and/or the target tissue type. Likewise, the insertion depth of the energy directors and the amount of power coupled to the energy directors is varied according to the treatment procedure and/or the target tissue type.

The application of power can be controlled either automatically or manually. When using automatic control, the process can be controlled according to a microprocessor control within the generator system itself or by at least one separate controller coupled among the components of the tissue ablation system. Further, the application of power to the energy directors can be controlled in response to measurements of temperature, impedance, and/or other feedback parameters associated with the ablation process.

When controlling ablation using temperature feedback, the temperature is increased at a rate approximately in the range of 25 degrees Celsius/minute to 100 degrees Celsius/minute to a temperature endpoint in the target tissue that is approximately in the range of 55 degrees Celsius to 110 degrees Celsius, but is not so limited. Using an appropriate rise in tissue temperature (25–100 degrees Celsius/minute) around an energy director, the highly conductive fluid inside the cells is released. This lowers the impedance around the energy director helping to prevent charring and allowing the continued (or increasing) flow of energy to the target tissue. This release is caused by the thermal damage to the cell wall. If the energy rise is too quick, the fluid will be quickly boiled or flashed off. This will result in no significant benefit and help to increase the tendency for tissue charring and a loss of ability to deliver energy to the target tissue.

In monitoring the application of power to the energy directors and the ablation process, a determination is made, either manually or automatically, as to whether the applied power has exceeded a desired value based on real-time temperature monitoring or other feedback parameters appropriate to the procedure. When it is determined that the power is exceeding the desired value, the power is reduced. If the power is within the prespecified parameters, other parameters can be monitored, such as impedance, time, and/or direct visualization of the coagulation plane. When these other parameters are found to be within acceptable limits, the power can be, increased further.

Additionally, the energy director temperatures or temperatures from satellite probes within and/or within proximity of the target tissue can be monitored. When the monitored temperatures remain within acceptable levels, the power can be increased or the flow of coolant modified.

Coupling power to the energy director guide/energy directors, at block 1306, results in generation of a plane of coagulated tissue in the target tissue, at block 1308. In an embodiment, a prespecified period of time for the application of power to the energy directors determines when the plane of coagulated tissue has been generated. Therefore, when the prespecified period of time elapses, the user stops the procedure. As described above, feedback of additional information can be used to determine successful completion of the procedure. Various portions of the procedure can be repeated, as appropriate to the target tissue, until the plane of coagulated tissue having the appropriate size and shape is generated, at block 1310.

Various alternative embodiments can simultaneously use any number of energy director guides/energy directors in a procedure in order to form volumes of coagulated tissue having shapes and sizes appropriate to the treatment procedure. Numerous alternatives would be recognized by those skilled in the art in view of the tissue ablation system described herein.

The tissue ablation system and associated processes described above can include other components in a variety of combinations. In addition to the display and controller described above, for example, a stereotactic frame or frameless navigator system may be used to direct and place the energy director guide/energy directors. Various guide tubes, templates, holding apparatus, arc systems, and spatial digitizers can also be used to assist in placement of the energy directors in the target tissue. Imaging modalities such as CT, MRI, ultrasound and the like can be used before, during, or after placement of the energy directors and/or creation of the ablation volume.

In addition to including numerous types and combinations of components, there are many alternative embodiments of the tissue ablation system components described above. Some of these alternatives include alternative embodiments of the energy director guide and the energy directors, as described below.

The energy director guide of one alternative embodiment includes a soft conformal bottom element that forms a conformal surface between the target tissue and the energy director guide. The conformal element takes on the shape of the surface of the underlying target tissue. Conformal bottom elements can be constructed from a variety of materials including silicone, biocompatible foam rubbers, and urethanes. Conformal bottom elements can also be formed with the use of inflated members.

The energy director guide of various alternative embodiments may take on a variety of shapes including, but not limited to, semi-circular, arcs, and angles. Many other shapes will be recognized by those skilled in the art.

Figure 14:
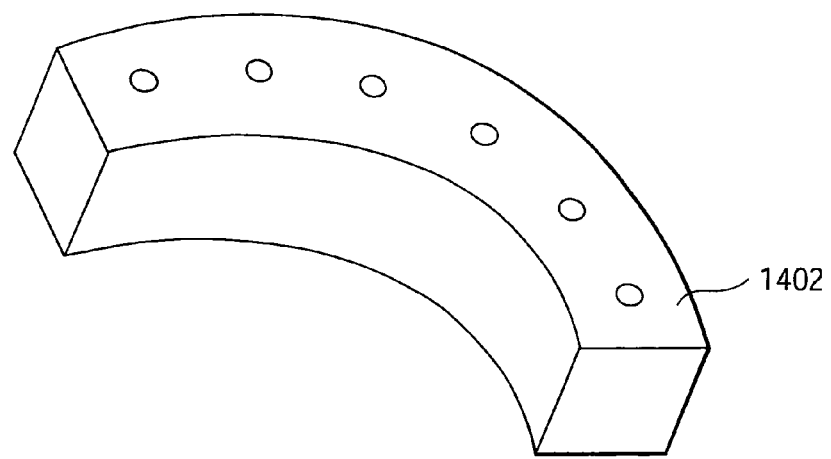
FIG. 14 shows a flexible or semi-flexible guide having flexibility in two planes, under an alternative embodiment.
Figure 15:
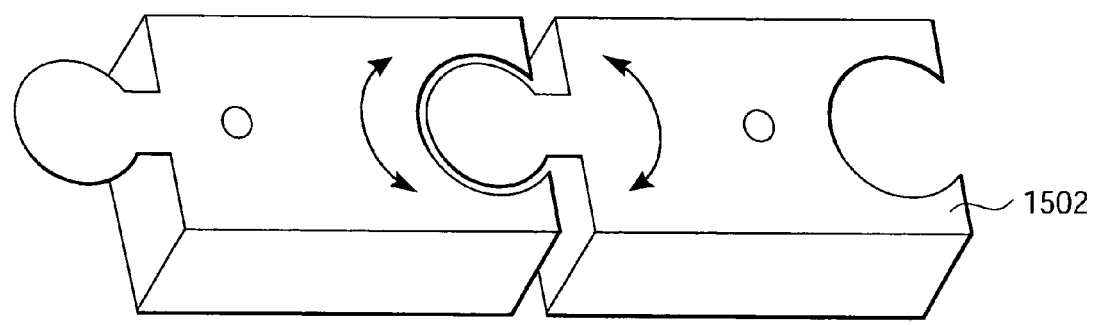
FIG. 15 shows a flexible or semi-flexible guide having flexibility in one plane, under another alternative embodiment.

FIG. 14 shows a flexible or semi-flexible guide 1402, under an embodiment. This flexible guide 1402 provides flexibility in two planes. FIG. 15 shows a flexible or semi-flexible guide 1502, under another alternative embodiment, that provides flexibility in one plane. These guides 1402 and 1502, while being configured to secure and couple power to the energy directors as described above with reference to FIGS. 2, 3, 7, 8, and 9, permit the user to alter the guide within limits to create a desired shape which, in turn, allows the resulting coagulation plane to match the desired outcome or avoid critical anatomical structures. Note that desired shapes including curved portions are formed from a series of coagulation planes having various dimensions, but the embodiment is not so limited.

These guides can be flexible or semi-flexible in a single or multiple planes. In a single plane, the guide can be shaped to the tissue targeted below the guide. With a second plane of flexibility, the guide can be used to contour to the shape of the surface or as necessary for location of the operative site.

Figure 16:
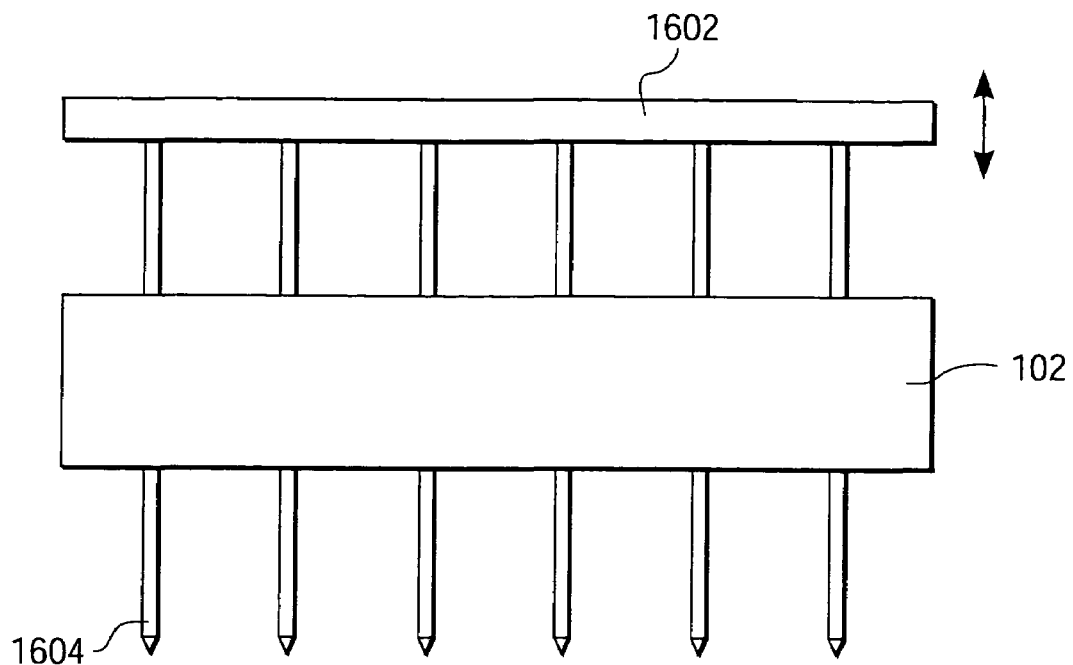
FIG. 16 is an energy director array including a joining member that provides for simultaneous insertion or retraction of energy directors into target tissue, under an embodiment.

FIG. 16 is an energy director array including a joining member 1602 that provides for simultaneous insertion or retraction of energy directors 1604 into target tissue, under an embodiment. The energy directors are connected to the joining member 1602 to allow for the simultaneous insertion or retraction of all energy directors 1604 via the energy director guide. As one example, all energy directors 1604 can be of the same length, thereby allowing the simultaneous insertion of all energy directors 1604 to a desired depth within the tissue. This is of benefit when a full thickness ablation plane is desired, there are no anatomical structures that would be contraindicated for the energy directors, and ease of use is important.

Figure 17:
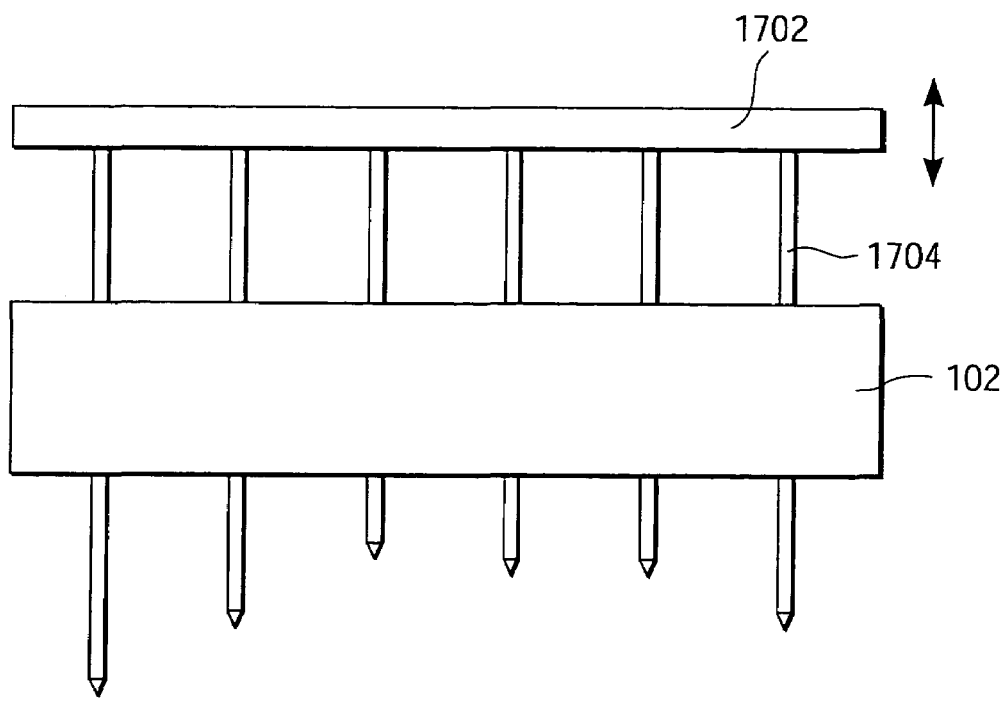
FIG. 17 is an energy director array including a joining member connected to energy directors, under an alternative embodiment.

FIG. 17 is an energy director array including a joining member 1702 connected to energy directors 1704, under an alternative embodiment. Select energy directors 1704 have non-uniform lengths as they are tailored to match the thickness and shape of the target tissue or organ and/or to avoid critical anatomical structures. The joining member 1702, therefore, supports the simultaneous insertion and withdrawal of all energy directors regardless of length while also supporting the avoidance of critical anatomical structures by the energy directors 1704.

The energy directors of an embodiment can be used with a variety of housings that enclose the energy directors prior to deployment into target tissue. Use of the housing minimizes unintentional deployment of the energy directors and reduces the potential for injury of a user or patient by the energy directors.

Many different types of energy directors can be used with the tissue ablation system of an embodiment. Descriptions follow of some example energy directors, but the embodiment is not so limited.

Figure 18:
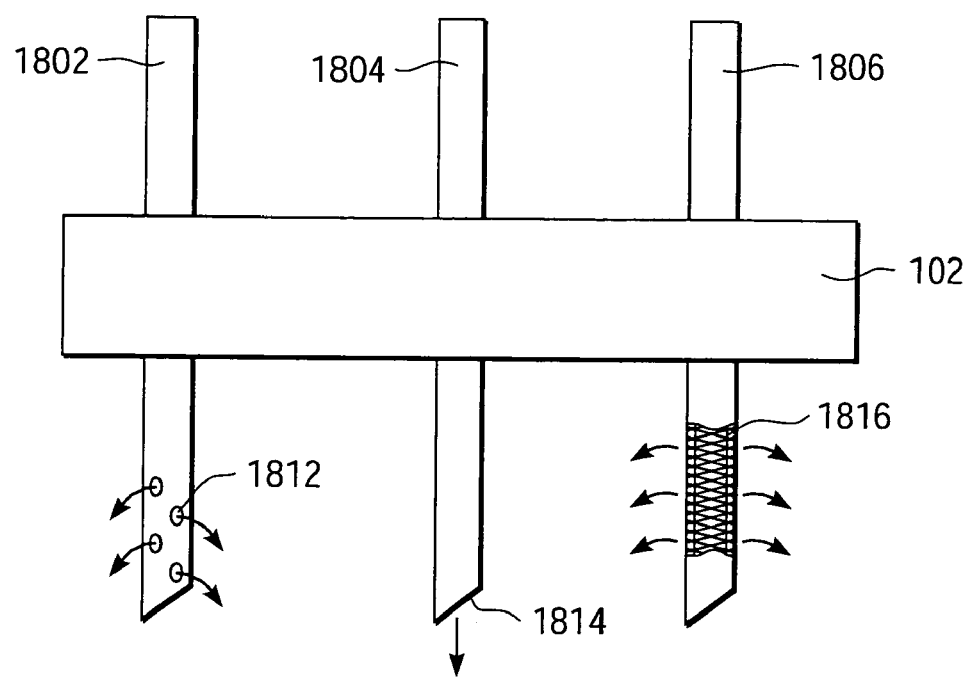
FIG. 18 shows energy directors supporting delivery of various agents into the target tissue, under an embodiment.

FIG. 18 shows energy directors 1802, 1804, and 1806 supporting delivery of various agents into the target tissue, under an embodiment. One type of energy director 1802 supports delivery of agents through a lumen in the energy director and apertures 1812 around the outer surface of the energy director 1802.

Another type of energy director 1804 supports delivery of agents through a lumen in the energy director and at least one aperture 1814 in the distal end of the energy director 1804. Yet another type of energy director 1806 supports delivery of agents through a lumen in the energy director in communication with a porous material 1816 around the outer surface of the energy director 1806.

The energy directors 1802, 1804, and 1806 support deliver of agents including, but not limited to, contrast agents used to better visualizes the detailed anatomy, sclerotic agents to help decrease the overall circulation in the target region, and chemotherapy agents for use as an adjunctive therapy. Still another example agent is a hyper- or hypo-tonic solution used to create a wet electrode.

Figure 19:
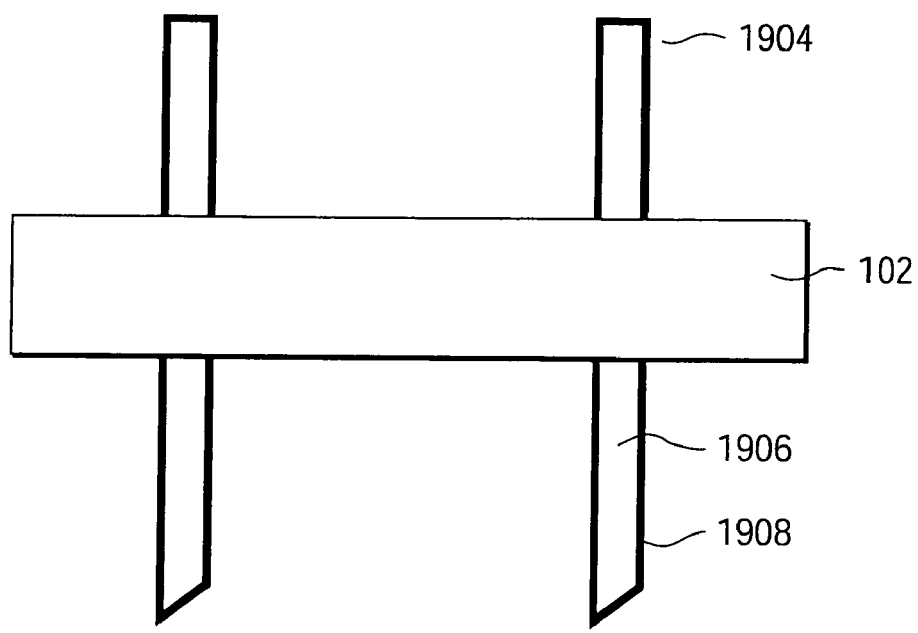
FIG. 19 shows energy directors that capacitively couple to target tissue, under an embodiment.

FIG. 19 shows energy directors 1904 that capacitively couple to target tissue, under an embodiment. In this embodiment the energy directors 1904 are fully, or near-fully insulated. An example of this configuration includes one or more conducting cores 1906 suitable for conducting energy, where the conducting core 1906 is fully or near fully insulated with an appropriate dielectric material 1908, coating, or sleeve. The thickness of coating 1908 varies according to the dielectric properties of the material used as the electrical insulator. Coating thicknesses of the various embodiments range from approximately 0.00005 inch to 0.001 inch, but are not so limited. In this configuration, the energy directors 1904 induce an energy flow into the target tissue. When appropriately applied, this energy would then cause the target tissue to heat and coagulate, as described above. The use of capacitive coupling in this form can increase the relatively low electrical impedance that results when several energy directors 1904 are used at a relatively close spacing.

The tissue ablation system of an embodiment includes one or more energy directors that support temperature monitoring within and/or around the target tissue. The temperature monitoring supported by the energy directors supports the real-time evaluation of an ablation procedure both outside and within the effected tissue zone. An example of this could be one or more thermocouples arranged in a configuration suitable for placement within the tissue, for example on and/or within an associated energy director, wherein the thermocouples couple to temperature monitoring equipment known in the art.

In generating coagulative ablation, the tissue ablation system and associated procedures of an embodiment deliver energy that results in tissue core temperatures approximately in the range between 65 degrees Celsius and 80 degrees Celsius in the coldest portions of the target tissue volume. The coldest portions of the target tissue volume are typically those areas that are the most distant from the energy directors or are thermally shielded from the effect of the energy directors by other anatomical structures.

Likewise, the tissue ablation system and associated procedures deliver energy that results in tissue core temperatures approximately in the range between 85 degrees Celsius and 105 degrees Celsius in the warmest portions of the target tissue volume. At temperatures below this, procedural times may be unnecessarily extended. At temperatures above this, instability may result due to the superficial charring caused by the excessive tissue heating. As noted herein, these conditions can be further mitigated with the use of other factors such has hypertonic agents. In particular, a continuous infusion of a 0.9% to 8% saline solution at an approximate rate of between 0.01 cc/min to 0.5 cc/min will aid in preventing tissue charring.

The temperature monitoring energy director provides the ability to control the energy delivered to the target tissue by controlling the energy with the use of a closed- or open-loop temperature feedback system. As such, optimum energy delivery can be achieved, thereby avoiding over delivery or under delivery of energy. Over delivery of energy can create superficially charred tissue resulting in a reduction or inability to deliver energy and an incomplete ablation. Under delivery of energy could significantly increase the procedural duration or even prevent the ability to complete the procedure. By controlling the transfer of energy to the target tissue in this manner, and by using non-stick surfaces such as fluoropolymers like polypropelene and parylene on the energy directors, charring can be minimized to produce optimal energy delivery and tissue ablation. In addition, the use of temperature monitoring also provides evidence and feedback as to the completion of the procedure, as described above.

As described above, the energy director guide of an embodiment configures the energy directors to provide approximately uniform power or energy distribution through the target tissue volume. Alternative embodiments of the tissue ablation system support the application of non-uniform energy distribution via either linear or non-linearly spaced arrays. This configuration monitors a parameter such as temperature, power, or impedance and, in response, controls the delivered energy to maintain the parameter(s) within a desired target range. By using individual energy channels for each bipolar pair, the energy can easily be altered as needed. For example, with a temperature goal of 80 degrees Celsius after initial ramps of 1.5 minutes to full power, or a predetermined maximum power, the time-temperature slopes are evaluated for each zone based on a predetermined ramp (approximately in the range of 50–80 degrees Celsius/minute). Based on the temperature ramp the power is altered to better match the desired rate.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," and words of similar import, when used in this application, shall refer to this application as a whole and not to any particular portions of this application.

The above description of illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings of the invention provided herein can be applied to other ablation systems, resection systems, and medical devices, not only for the tissue ablation system described above.

The elements and acts of the various embodiments described above can be combined to provide further embodiments. These and other changes can be made to the invention in light of the above detailed description.

All of the above references and United States patent applications are incorporated herein by reference. Aspects of the invention can be modified, if necessary, to employ the systems, functions and concepts of the various patents and applications described above to provide yet further embodiments of the invention.

In general, in the following claims, the terms used should not be construed to limit the invention to the specific embodiments disclosed in the specification and the claims, but should be construed to include all processing systems that operate under the claims to provide a method for compressing and decompressing data files or streams. Accordingly, the invention is not limited by the disclosure, but instead the scope of the invention is to be determined entirely by the claims.

While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

What we claim is:

1. A tissue ablation system comprising:
    an energy source;
    two or more pairs of bipolar energy directors configured for insertion into a volume of biological tissue; and
    an energy director guide that configures the energy directors to generate at least one plane of coagulated tissue in the volume of tissue by coupling energy from the energy source to the volume of tissue, wherein the energy director configuration results in approximately uniform energy distribution through the tissue volume;
    wherein the guide includes a series of channels that receive the energy directors in an alternating polarity series, wherein spacing among the channels varies according to a number of pairs of energy directors received in the energy director guide so that relative spacing among the center-most channels is largest and relative spacing among the end-most channels is smallest; and
    wherein the guide independently couples the energy source to each of the energy directors.

2. The system of claim 1, wherein the energy source includes a radio frequency generator.

3. The system of claim 1, wherein the guide further secures a selected depth position of the energy directors in the tissue volume.

4. The system of claim 1, wherein the two or more pairs of bipolar energy directors include three pairs of bipolar energy directors.

5. The system of claim 1, wherein the two or more pairs of bipolar energy directors include four pairs of bipolar energy directors.

6. The system of claim 1, wherein the energy directors further include at least one component selected from among temperature sensors, thermocouples, infusion components, and optical tissue monitors.

7. The system of claim. 1, further comprising at least one controller coupled among the energy source and the bipolar energy directors, wherein the controller supports automatic control of energy delivery to each of the bipolar energy directors.

8. The system of claim 1, wherein the energy directors are inserted to independently variable depths in the volume of biological tissue.

9. The system of claim 1, wherein the energy directors are internally cooled.

10. The system of claim 1, further comprising at least one housing, wherein the housing includes the energy directors and is configured to couple to the energy director guide, wherein the energy directors are deployed from the housing and inserted into the volume of biological tissue.

11. The system of claim 1, wherein the uniform energy distribution includes uniform current density.

12. The system of claim. 1, wherein the alternating polarity series includes at least one electrode of a positive polarity in series with at least one electrode of a negative polarity.

13. A system for generating at least one plane of coagulated tissue in a volume of biological tissue, the system comprising at least one guide including a series of channels that configure two or more sets of bipolar electrodes in an alternating polarity series, wherein spacing among the channels varies according to a total number of bipolar electrodes received in the guide so that relative spacing among the center-most channels is largest and relative spacing among the end-most channels is smallest, wherein the guide secures a selected position of each of the electrodes in the target biological tissue and couples each bipolar electrode to at least one energy source.

14. A method for generating at least one plane of coagulated tissue in biological tissue, comprising:
    positioning an electrode guide on a surface of a biological tissue region that includes a target tissue volume, wherein the electrode guide includes a series of channels that configure two or more pairs of bipolar electrodes in an alternating polarity series, wherein spacing among the channels varies according to a total number of bipolar electrodes received in the guide so that relative spacing among the center-most channels is largest and relative spacing among the end-most channels is smallest;
    securing the bipolar electrodes at a selected depth in the target tissue volume using the electrode guide;
    coupling at least one energy source to the bipolar electrodes using the electrode guide and providing approximately uniform energy distribution through the target tissue volume; and
    generating the at least one plane of coagulated tissue in the target tissue volume.

15. The method of claim 14, further comprising infusing a solution into the target tissue volume via at least one of the bipolar electrodes, wherein the solution is at least one of a hyper-tonic solution, a hypo-tonic solution, a contrast agent, a sclerotic agent, and a chemotherapy agent.

16. A method for generating a plane of coagulated tissue in biological tissue, comprising:
   positioning an electrode guide in proximity to a target tissue volume; inserting two or more pairs of bipolar electrodes into the target tissue volume in a series of alternating polarity via the electrode guide;
   securing the bipolar electrodes at a selected depth in the target tissue volume using components of the electrode guide;
   coupling at least one energy source to the target tissue volume via the bipolar electrodes;
   controlling energy delivery to effect approximately uniform energy distribution through the target tissue volume, wherein a target temperature in the target tissue volume is greater than a temperature approximately in the range of 55 degrees Celsius to 60 degrees Celsius; and
   generating the plane of coagulated tissue in the target tissue volume.

17. The method of claim 16, wherein the target temperature is measured at one or more of the electrodes.

18. The method of claim 16, wherein the target temperature is measured at one or more points in the target tissue volume.

19. A tissue ablation apparatus for use in a resection procedure of tissue within a mammalian body, comprising:
   a support body having a first and second end portions and a surface extending between the first and second end portions; and
   a plurality of at least first, second and third elongate radio frequency electrodes carried by the support body and extending from the surface in spaced-apart positions between the first and second end portions, the first and second electrodes being spaced apart by a first distance and the second and third electrodes being spaced apart by a second distance different than the first distance, the first and second distances being chosen so that when the first, second and third electrodes are disposed in the tissue the energy distribution between the first and second electrodes and the energy distribution between the second and third electrodes are approximately uniform.

20. The tissue ablation apparatus of claim 19, wherein the first, second and third electrodes are parallel.

21. The tissue ablation apparatus of claim 19, wherein each of the first, second and third electrodes is a needle electrode.

22. The tissue ablation apparatus of claim 19, further comprising a fourth elongate radio frequency electrode spaced from the third electrode by a third distance different from the first and second distances, the third distance being chosen so that when the second, third and fourth electrodes are disposed in the tissue the energy distribution between the second and third electrodes and the energy distribution between the third and fourth electrodes are approximately uniform.

23. The tissue ablation apparatus of claim 19, further comprising a radio frequency generator coupled to the first and second electrodes for supplying a first potential to the first electrode and a second potential to the second electrode.

24. The tissue ablation apparatus of claim 19, further comprising a radio frequency generator coupled to the radio frequency electrodes for supplying a first potential to the first and second electrodes and a second potential to the third and fourth electrodes.

25. A method for resecting a portion of a target organ within a mammalian body with a support body having a first and second end portions and a surface extending between the first and second end portions and a plurality of electrodes extending from the surface and spaced sequentially between the first and second end portions, comprising:
   positioning the electrodes in the vicinity of the target organ;
   extending the electrodes into the target organ so that relative lateral spacing among center-most electrodes of the plurality of electrodes is larger than relative lateral spacing among end-most electrodes of the plurality of electrodes;
   supplying a first potential of radio frequency energy to a first group of the plurality of electrodes and a second potential of radio frequency energy to a second group of the plurality of electrodes so that radio frequency energy travels between the first and second groups of electrodes and thus forms a wall of ablated tissue in the target organ; and
   incising the target organ in the vicinity of the wall of ablated tissue to resect the portion of the target organ.

26. The method of claim 25, further comprising estimating a transverse dimension of the target organ and sizing the electrodes as a function of the transverse dimension to prevent the electrodes from extending beyond the target organ when the surface is substantially flush with the target organ.

27. The method of claim 25, further comprising separating the target organ from an adjacent organ to prevent the electrodes from piercing the adjacent organ when the electrodes are extended into the target organ.

28. The method of claim 27, further comprising placing a shield between the target organ and the adjacent organ to protect the adjacent organ from the electrodes.

* * * * *